US010235584B2

(12) United States Patent
Leizerson

(10) Patent No.: US 10,235,584 B2
(45) Date of Patent: Mar. 19, 2019

(54) SYSTEM FOR OBJECT AUTHENTICITY DETECTION INCLUDING A REFERENCE IMAGE ACQUISITION MODULE AND A USER MODULE AND METHODS THEREFOR

(71) Applicant: ELBIT SYSTEMS LAND AND C4I LTD., Netanaya (IL)

(72) Inventor: Ilya Leizerson, Netanaya (IL)

(73) Assignee: ELBIT SYSTEMS LAND AND C4I LTD., Netanaya (IL)

( * ) Notice: Subject to any disclaimer, the term of this patent is extended or adjusted under 35 U.S.C. 154(b) by 0 days.

(21) Appl. No.: 15/763,804

(22) PCT Filed: May 24, 2017

(86) PCT No.: PCT/IL2017/050581
§ 371 (c)(1),
(2) Date: Mar. 27, 2018

(87) PCT Pub. No.: WO2017/208225
PCT Pub. Date: Dec. 7, 2017

(65) Prior Publication Data
US 2019/0026581 A1    Jan. 24, 2019

(30) Foreign Application Priority Data

May 30, 2016    (IL) .......................................... 245932

(51) Int. Cl.
*G06K 9/20*    (2006.01)
*G02B 27/10*    (2006.01)
(Continued)

(52) U.S. Cl.
CPC ........... *G06K 9/2027* (2013.01); *G01N 21/47* (2013.01); *G02B 27/10* (2013.01); *G06K 9/2036* (2013.01);
(Continued)

(58) Field of Classification Search
CPC .... G02B 27/00; G02B 5/1828; G02B 5/1857; G06K 9/2027; G06K 9/2036;
(Continued)

(56) References Cited

U.S. PATENT DOCUMENTS 2,488,146 A    11/1949  Steinhaus
6,020,954 A     2/2000  Aggarwal
(Continued)

OTHER PUBLICATIONS

International Search Report dated Sep. 11, 2017 for International Application No. PCT/IL2017/050581, 3 pages.
(Continued)

*Primary Examiner* — Jingge Wu
(74) *Attorney, Agent, or Firm* — Knobbe, Martens, Olson & Bear, LLP

(57) ABSTRACT

A system for determining the authenticity of an object including a reference-image acquisition module for acquiring a reference-image. The reference-image acquisition module includes a light-source, an imager including an imaging-sensor, and a database coupled with the imager for storing the reference-image. The light-source directs circumferential-light toward an authentication-region on the object. The circumferential-light is at least one of collimated and telecentric. The circumferential-light impinges on the authentication-region from a plurality of different azimuthal directions and at a predetermined oblique angle relative to the normal of a plane defined by said object. A portion of the circumferential-light is reflected from the authentication-region toward a specular reflection region and another portion is scattered from the authentication-region. The imager is focused on the authentication-region and acquires a reference-image. The reference-image is a focused image of the scattered light. The reference-image includes image features related to surface features scattering phenomena of the authentication-region.

13 Claims, 20 Drawing Sheets

(51) Int. Cl.
   *G01N 21/47* (2006.01)
   *G06T 7/00* (2017.01)
   *H04N 5/225* (2006.01)

(52) U.S. Cl.
   CPC ...... *G06T 7/0004* (2013.01); *G01N 2021/479* (2013.01); *H04N 5/2256* (2013.01)

(58) Field of Classification Search
   CPC .... G03H 2001/0212; G03H 2001/0467; G06T 7/0004; G01N 21/47
   See application file for complete search history.

(56) References Cited

U.S. PATENT DOCUMENTS

| | | | |
|---|---|---|---|
| 6,842,298 B1 | 1/2005 | Shafer et al. | |
| 7,136,159 B2 | 11/2006 | Tsai et al. | |
| 7,136,234 B2 | 11/2006 | Shafer et al. | |
| 7,502,177 B2 | 3/2009 | Shafer et al. | |
| 7,728,968 B2 | 6/2010 | Tsai et al. | |
| 7,925,056 B2 | 4/2011 | Presura et al. | |
| 8,781,153 B2 | 7/2014 | Sharma et al. | |
| 9,208,394 B2* | 12/2015 | Di Venuto Dayer | G06K 9/00577 |
| 9,934,418 B2* | 4/2018 | Mienko | G06F 3/0421 |
| 2003/0156294 A1 | 8/2003 | D'Agraives et al. | |
| 2004/0095573 A1 | 5/2004 | Tsai et al. | |
| 2005/0153559 A1 | 7/2005 | Shafer et al. | |
| 2006/0091333 A1 | 5/2006 | Cochran et al. | |
| 2006/0104103 A1 | 5/2006 | Colineau et al. | |
| 2007/0058260 A1* | 3/2007 | Steenblik | B42D 25/29 359/626 |
| 2007/0121107 A1 | 5/2007 | Tsai | |
| 2007/0171547 A1 | 7/2007 | Shafer et al. | |
| 2008/0037131 A1* | 2/2008 | Steenblik | B44F 1/10 359/619 |
| 2008/0146952 A1 | 6/2008 | Presura et al. | |
| 2008/0149700 A1 | 6/2008 | Tuyls et al. | |
| 2011/0080603 A1 | 4/2011 | Horn et al. | |
| 2012/0237731 A1* | 9/2012 | Boegli | B82Y 10/00 428/156 |
| 2012/0243094 A1* | 9/2012 | Boegli | B44B 5/026 359/567 |
| 2012/0257046 A1* | 10/2012 | Mueller | G06K 9/00013 348/135 |
| 2013/0212027 A1 | 8/2013 | Sharma et al. | |
| 2014/0055775 A1 | 2/2014 | Imai et al. | |
| 2014/0193046 A1* | 7/2014 | Mason | G06K 9/00617 382/117 |
| 2014/0205153 A1 | 7/2014 | Sharma et al. | |

OTHER PUBLICATIONS

Written Opinion of the International Searching Authority dated Sep. 11, 2017 for International Application No. PCT/IL2017/050581, 4 pages.
"Dark Field Illumination", Stemmer Imaging Ltd. https://www.stemmer-imaging.co.uk/en/knowledge-base/dark-field-illumination/.
I Craddock, P.T. (Paul T.), "Scientific Investigation of Copies, Fakes and Forgeries", 2009, Elsevier Ltd.
Zhang J., P.P.L. Regtien, "Illumination Methods for Optical Wear Detection", Measurement Science Review, vol. 7, Section 3, No. 3, 2007, pp. 37-41.
Impact case study (REF3b), Imperial College London, "P12—Anticounterfeiting: Ingenia Technology Ltd and Laser Surface Authentication" http://impact.ref.ac.uk/CaseStudies/CaseStudy.aspx?Id=42251.
Chia-Hung Yeh, Po-Yi Sung, Chih-Hung Kuoand Ruey-Nan Yeh "Robust laser speckle recognition system for authenticity identification", Oct. 22, 2012 / vol. 20, No. 22/ Optics Express, 2012 OSA.
Ashlesh Sharma et al, "Microscopic paper fingerprinting" SPIE, CCS'11, Oct. 17-21, 2011, Chicago, Illinois, USA. Copyright 2011 ACM 978-1-4503-0948-6/11/10.

* cited by examiner

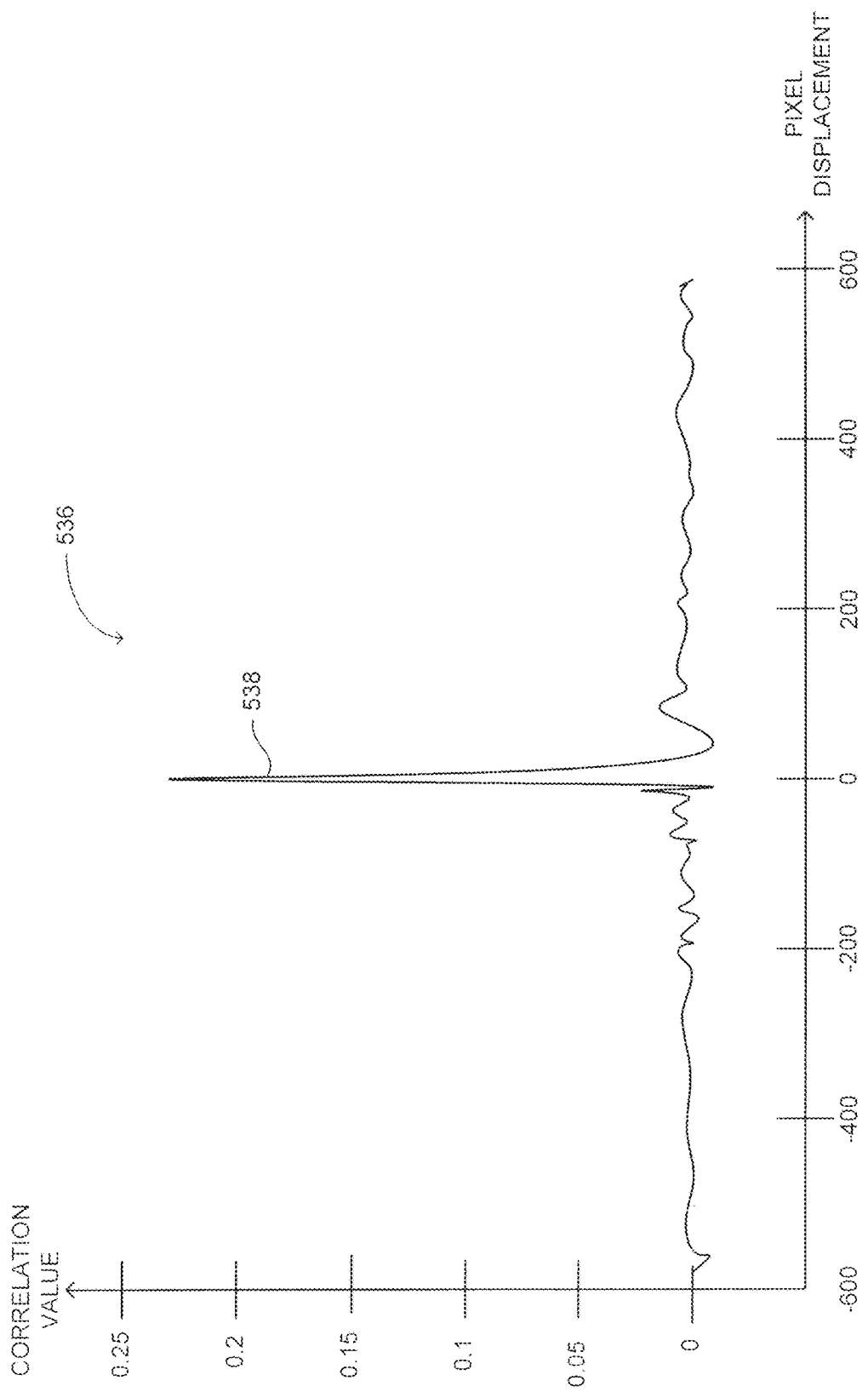

SYSTEM FOR OBJECT AUTHENTICITY DETECTION INCLUDING A REFERENCE IMAGE ACQUISITION MODULE AND A USER MODULE AND METHODS THEREFOR

CROSS REFERENCE TO RELATED APPLICATIONS

This application is the U.S. National Phase Application under 35 U.S.C. § 371 of International Application No. PCT/IL2017/050581, filed May 24, 2017, designating the U.S. and published as WO2017/208225 A1 on Dec. 7, 2017 which claims the benefit of Israel Patent Application No. 245932, filed May 30, 2016, which is hereby incorporated by reference in their entirety.

FIELD OF THE DISCLOSED TECHNIQUE

The disclosed technique relates to imaging and image processing techniques in general, and to systems and methods for detecting authenticity of objects according to acquired images thereof, the images at least including image features related to surface features scattering phenomena, in particular.

BACKGROUND OF THE DISCLOSED TECHNIQUE

Counterfeiting of objects in general, affects the income of manufacturers which manufacture an original object and may also affect the income of distributors wholesalers and retailers. The market of counterfeited objects is estimated to be on the order of hundreds of billions of dollars per year. Methods, devices and systems for detecting counterfeited objects are known in the art. For example, electronic circuits (e.g., passive or active Radio Frequency Identification—RFID circuits) are incorporated in to the object. As a further example, expendable tags with unique patterns such as holograms, tags with spectral patterns and the like are attached to the object. These methods, devices and systems are specifically designed and may be subjected to counterfeiting themselves. Alternatively, systems and methods which analyze an image of the object surface are also employed. For example, such systems and methods acquire and analyze a speckle pattern of the objects or regions in the objects to determining the authenticity of the object. Such methods employ the object surface illuminated with light for creating an optical interferogram known as a speckle pattern.

U.S. Application Publication 2006/0104103 to Colineau et al, entitled "Method for Optical Authentication and Identification of Objects and Device Therefor" directs to a system and a method in which a coherent light illuminates a partially scattering surface of reference objects under specified illumination conditions and record the speckle patterns obtained for various nominal values of illumination parameters. Then, objects are illuminated and their images are captured under the similar nominal conditions and each obtained speckle pattern is compared with a recorded speckle pattern. The system directed to by Collineau et al includes an optical recording device with laser source, a storage device and an optical reading device with laser source, the parameters of the optical devices being modifiable. The modifiable parameters of the optical devices include at least one of the wavelength, direction of emission, focusing of the laser beam, position of the laser source, inclination and position of the object with respect to the laser beam. According to an embodiment of the system directed to by Collineau et al, the system verifies that value of a given parameter may be drawn randomly from the span of admissible values (for example in the case of a particular position of the reading system with respect to the object), the signal observed is indeed the one that is expected. It is thus possible to choose the security level desired.

U.S. Patent Application Publication 2014/0205153 to Sharma et al, entitled "Systems, Methods and Computer-Accessible Mediums of Authentication and Verification of Physical Objects" directs to a method for authenticating a physical object. Initially, an image of a marked or unmarked portion of the physical object is acquired under white light illumination. Then a first microscopic image or video of a region of the objects is stored. This first microscopic image includes a texture speckle pattern. A descriptor is computed using object invariant gradient histogram algorithm or a combination of a Gabor transform and a Principal Component Analysis procedure. When verifying the authenticity of the physical object, a predetermined region is chosen and an image or video of the physical object that is acquired by a microscope (e.g., a USB microscope). The microscope can be a handheld device, such a cellular telephone integrated with a microscope, or a digital camera integrated with a microscope. The second microscopic image or video is stored and a low dimensional representation of this image is computed by employing, for example, the invariant Gabor Principal Component Analysis. Then, the first microscopic image and the second microscopic image are compared. This comparison is be performed by matching the descriptors for example according to the Euclidean distance between the descriptors. If a similarity between the first and second speckle patterns equals or exceeds a predetermined amount, then the physical object is determined to be authentic, else the physical object is not authentic.

U.S. Pat. No. 6,020,954 to Aggarwal entitled "Method and Associated Appartus for the Standardized Grading of Gemstones" directs to a system for determining the spectral response of a gemstone which is subjected to a plurality of incident light sources. In the system directed to Aggarwal, an image acquires an image of the illuminated gemstone and a processor compares the acquired image to a reference image and grades the inspected gemstone. In the system directed to by Aggarwal, a ring light illuminates the gemstone to detect surface scratches, facet structures, and to perform color analysis of dark stones.

SUMMARY OF THE PRESENT DISCLOSED TECHNIQUE

It is an object of the disclosed technique to provide novel systems for determining authenticity of an object which includes a reference image acquisition module and a user module. In accordance with the disclosed technique, there is thus provided system for determining the authenticity of an object including a reference image acquisition module for acquiring a reference image for object authenticity detection. The reference image acquisition module includes a light source, an imager and a database. The imager includes an imaging sensor. The database is coupled with the imager. The light source directs circumferential light toward an authentication region on the object. The circumferential light is at least one of collimated and telecentric. The circumferential light impinges on the authentication region from a plurality of different azimuthal directions and at a predetermined oblique angle relative to the normal of a plane defined by said object. A portion of the circumferential light is reflected from the authentication region toward a specular reflection region. Another portion of the circumferential light is scattered from the authentication region. The imager is substantially focused on the authentication region and acquires at least one reference image. The reference image is a focused image of the scattered light. The reference image includes image features related to surface features scattering phenomena of the authentication region. The specular reflection region and a region defined by the imaging sensor are mutually exclusive in space. The database stores the reference image.

BRIEF DESCRIPTION OF THE DRAWINGS

The disclosed technique will be understood and appreciated more fully from the following detailed description taken in conjunction with the drawings in which:

FIG. 7H is a schematic illustration of a graph exhibiting a correlation function between images also in accordance with another embodiment of the disclosed technique;

DETAILED DESCRIPTION OF THE EMBODIMENTS

Figure 1:
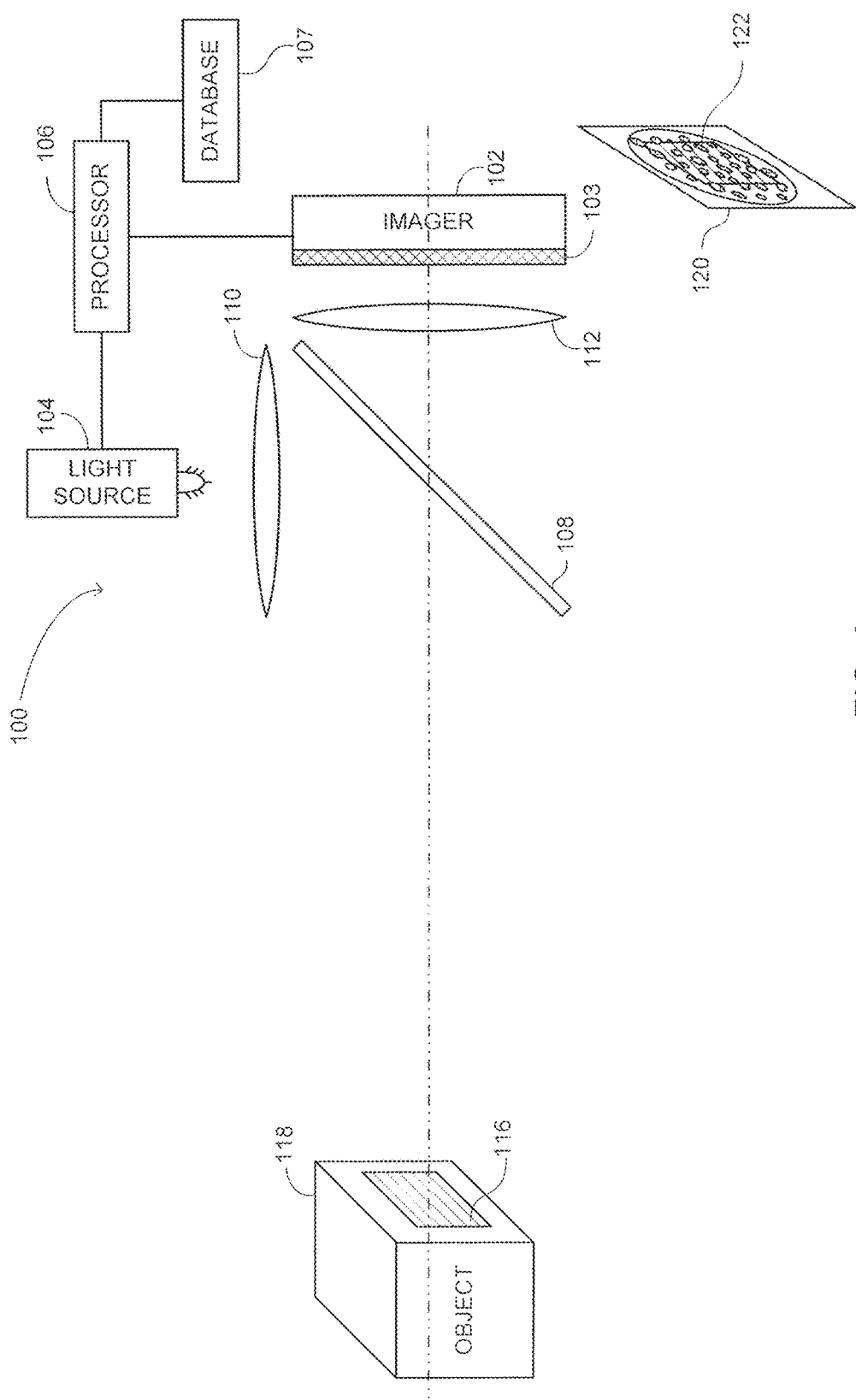
FIG. 1, is a schematic illustration of a system for determining authenticity of an object, constructed and operative in accordance with an embodiment of the disclosed technique.

The disclosed technique overcomes the disadvantages of the prior art by providing a system for identifying objects and for determining authenticity of objects. According to the disclosed technique, a light source emits light toward an authentication region on the object. The authentication region exhibits surface features and material characteristics. The term 'surface features' relates herein to the physical texture, roughness and irregularities such as scratches, cracks. The term 'material characteristic' relates herein to spectral reflectivity (i.e., ratio between the power of the scattered and reflected light to the power of the incident light for each wavelength), spectral absorption (i.e., ratio between absorbed and incident light power), polarization (i.e., the change in polarization state of the scatter and reflected light with respect to the incident light). The surface features affect the reflection and scattering of light from the surface of the authentication region. The light impinges on the surface of the authentication region and scatters and reflects therefrom. The term 'reflected light' relates herein to light which is specularly deflected from the surface of the authentication region (i.e., the deflection angle of the light from the authentication region is equal to the incident angle of the light on the authentication region). The term 'scattered light' relates herein light which is diffusively deflected from the surface of the authentication region.

At least a portion of the scattered light from the authentication region impinges on an imaging sensor of an imager. The imager acquires at least one substantially focused (i.e., an image acquired within the depth of focus of the imager) image of the authentication region. The acquired image at least includes image features related to surface features scattering phenomena. These image features are for example speckle pattern or a representation of the surface irregularities (e.g., scratches, cracks or protrusions). In other words, the image features are identifiable in the image.

A processor determines the correspondence between the acquired image or images and stored image or images, which also correspond to the same authentication region or authentication region type. The processor identifies the object as authentic when the acquired image or images corresponds to the stored image or images. The Processor identifies object as non-authentic when the acquired image or images do not correspond to the stored image or images.

According to one embodiment of the disclosed technique light impinges on the authentication region at an oblique angle relative to the normal of the object plane (i.e., at the authentication region). This oblique angle should be small enough to maintain the coherency of the incident light within a region observed by a single pixel as further explained below. Furthermore, the region defined by the imaging sensor and a specular reflection region are mutually exclusive in space. The acquired image includes image features related to surface features scattering phenomena. As mentioned above, these image features are for example speckle pattern or a representation of the surface irregularities (e.g., scratches, cracks or protrusions). Specifically, the representations of the surface irregularities in the acquired image in addition to the speckle pattern further reduce the probability of false detection of a non-authentic object relative to the probability of false detection when employing an image which does not include representations of the surface irregularities. Illuminating the authentication region at an oblique angle enables employing specularly reflected surfaces for counterfeit detection such as Identification Cards, credit cards, glasses, partially reflecting parts of clothes and the like.

According to a further embodiment of the disclosed technique, the emitted light exhibits emitted spectral scheme. The emitted spectral scheme includes at least two wavelengths over at least two respective emitted spectral ranges. The emitted light impinges on the authentication region and scatters and reflects therefrom over a scattered spectral range. The light scattered from each area observed by each pixel on the authentication region, exhibits a respective scattered spectral scheme. The intensity corresponding to each wavelength in each scattered spectral scheme depends on the surface feature of that area and material characteristics thereof. At least a portion of the scattered light from the authentication region impinges on an imaging sensor of an imager. The imager acquires at least one focused image of the authentication region resulting from the scattered light over the spectral response of the imager. The spectral response of the imager includes at least two spectral ranges. Each acquired spectral range is associated with a corresponding spectral authentication image. In other words, the acquired image is comprised of the spectral authentication images. Each spectral authentication image includes respective image features (i.e., related to surface features scattering phenomena), that are related to the spectral schemes of the pixels (i.e., within the corresponding spectral range thereof). The processor determines correspondence between at least one spectral authentication image, and a stored spectral authentication image which also correspond to the same spectral range, and determines the authenticity of the object accordingly. Employing at least two spectral authentication images corresponding to two respective spectral ranges reduces the probability of false detection relative to the probability of false detection when only a single image is employed.

In general, the authentication region exhibits scattering characteristics which depend on the wavelength or wavelengths of the light incident thereon. These wavelength dependent scattering characteristics are also referred to herein as 'the spectral response of the scattered light'. The scattering characteristics are related to the surface features and material characteristics of the authentication region at the area observed by each pixel. Consequently, light exhibiting different wavelengths, incident on the authentication region, shall result in different speckle patterns. In other words, the position and shape of the dark and bright areas in the speckle patterns can vary for different wavelengths and spectral schemes. Surface irregularities also exhibit respective wavelength dependent scattering characteristics. This spectral response of the scattered light is related to the structure of these surface irregularities. Therefore, an image based on the scattered light exhibits image features which are related to the surface features scattering phenomena.

A user seeking to verify or determine the authenticity of an object and employing a system according to the disclosed technique, directs the imager toward the authentication region, the system provides the user with an indication (e.g., visual indication via a display or an audio indication) via a display that the object is authentic.

Reference is now made to FIG. 1, which is a schematic illustration of a system, generally referenced 100, for determining authenticity of an object, constructed and operative in accordance with an embodiment of the disclosed technique. System 100 is employed in a user module when a user seeks to verify or determine the authenticity of an object. System 100 includes an imager 102, a light source 104, a processor 106, a database 107. Imager 102 includes an imaging sensor 103. System 100 includes a light source optics 110 and imaging optics 112 and optionally includes a beamsplitter 108. Processor 106 is coupled with the imager 102, with light source 104 and with database 107. Light source optics 110 is optically coupled with light source 104 and with beamsplitter 108. Imaging optics 112 is optically coupled with imager 102 and with beamsplitter 108. Imaging optics 112 is optically coupled with beamsplitter 108. The term 'optically coupled' refers herein to two elements, a first element and a second element, both located on the same optical path of a photon, the photon exiting one element reaches the second element even if that photon passed other optical elements (e.g., lenses, optical relays, beamsplitters, diffusers, grids, prisms, diffractors, mirros), which are located on the optical path between the first element and the second element.

Imaging sensor or sensors 103 (e.g., Charged Coupled Device—CCD sensor or Complementary Metal Oxide Semiconductor—CMOS sensor), exhibiting sensitivity at respective spectral band or bands. For example, imaging sensor 103 may be sensitive in the visible spectral band and capable of acquiring a color image in the Red, Green and Blue color space (i.e., imager 102 is an RGB camera). For example, imaging sensor 103 may be sensitive in the visible spectral band and capable of acquiring a monochrome image. As a further example, imager 102 may be a multi-spectral imager, including two or more sensors each exhibiting sensitivity at respective spectral band. For example, these sensors may be an infrared (IR) sensor exhibiting sensitivity in the IR band, a sensor exhibiting sensitivity in the visible band (i.e., either a monochrome sensor or a color sensor) and an Ultraviolet (UV) sensor exhibiting sensitivity in the UV band. Light source 104 emits light (i.e., electromagnetic energy) in selected spectral bands or portions thereof. Light source 104 may be, for example, a Light Emitting Diode (LED) or LEDs, a fluorescent lamp or lamps, tungsten lamps or lamps, a UV lamp and the like. For example, light source 104 may emit light only in the Near Infrared (NIR) and UV bands and imager 102 thus acquire images in the NIR and UV bands. A spectral filter corresponding to the desired spectral band or a number of such filters can be mounted on light source 104. Alternatively, light source 104 may include several light emitters, each emitting light in a corresponding wavelength or wavelengths over a corresponding spectral band. The light emitters may emit the light simultaneously or sequentially. In general, the spectral response of imager 102 at least partially overlaps with spectral bands of the light emitted by light source 104.

Light source 104 emits light via light source optics 110 toward beamsplitter 108. When light source 104 includes several light emitters, all light emitters emit the light substantially toward the same direction. The light emitted by light source 104 may be strongly coherent light (e.g., laser light), partially coherent light or low-coherent light such as a LED. In general, light coherency relates to the correlation between the phases of the various wavefronts of the light over distance or time. The light emitted by light source 104 may further be monochromatic light or multi-chromatic light.

Beamsplitter 108 directs the light toward an authentication region 116 of an object 118. Authentication region 116 exhibits light reflection and scattering characteristics corresponding to the surface and the surface texture thereof. The light scattered from authentication region 116 is directed via beamsplitter 108 and imaging optics 112 toward imager 102 and impinge on imaging sensor 103. Imager 102 acquires at least one focused image 120 of authentication region 116. The acquired focused image 120 of authentication region 116 at least includes image features 122, relating to surface features of authentication region 116. These image features 122 are for example speckle pattern or images of surface irregularities such as scratches, protrusions and the like or both.

Processor 106 determines the correspondence between the acquired image or images and stored image or images, which are stored in database 107 and also correspond to the authentication region or the authentication region type of the object. Processor 106 determines the correspondence between the acquired image and a stored image, for example, by determining the correlation between the two images. For example, processor 106 may determine the correspondence between corresponding parts of the acquired and stored spectral authentication images by determining the correlation between selected quadrants of the images. Thus, even if a portion of authentication region 116 is damaged, or if a portion of the acquired image is corrupt, processor 106 can still determine the correspondence between the images. Processor 106 determines that two images correspond to one another when the maximum value of the normalized correlation is above a predetermined threshold. This threshold may be defined relative to the maximum possible correlation value (i.e., relative to 1 when the correlation is normalized) (e.g., the threshold may be a fraction of the maximum possible correlation value). As a further example, the threshold may be defined relative to the variance or the mean of the correlation values, at a determined segment of pixel shifts (i.e., a segment in the horizontal axis of the correlation function), the determined segment being different from the segment in which the maximum value is located (e.g., the threshold is defined as a multiple of the determined variance or mean). Furthermore, Hough Transform technique can be employed for identifying scratches in the acquired image or images by detecting lines in images which corresponding to these scratches. Processor 106 identifies object 118 as authentic when the acquired image or images corresponds to the stored image or images. Processor 106 identifies object 118 as non-authentic when the identified spectral authentication image or images do not correspond to the stored spectral authentication image or images. In general, the authentication region may be a part of the object or appended thereto (e.g., a sticker).

The system according to the disclosed technique is generally employed with various objects exhibiting various surfaces with various surface characteristics, for example, completely scattering surfaces, partially reflecting surfaces, specular reflecting surfaces, as can be seen on various objects (e.g., such as credit cards, luxury watches). For the system to be employed with a variety of surfaces, the system should be configured such that the reflected light does not impinge the imaging sensor. To that end, in a system according to another embodiment of the disclosed technique, light, originating from telecentric or collimated light source, impinges on the authentication region at an oblique angle relative to the normal to the object plane. Furthermore, the region defined by the imaging sensor and a specular reflection region are mutually exclusive in space (i.e., the region defined by the imaging sensor and a specular reflection region do not overlap) as further explained below. Illuminating the surface with collimated or telecentric light and the non-overlap between the region defined by the imaging sensor and a specular reflection region is referred to herein as 'oblique illumination imaging'

Figure 2A:
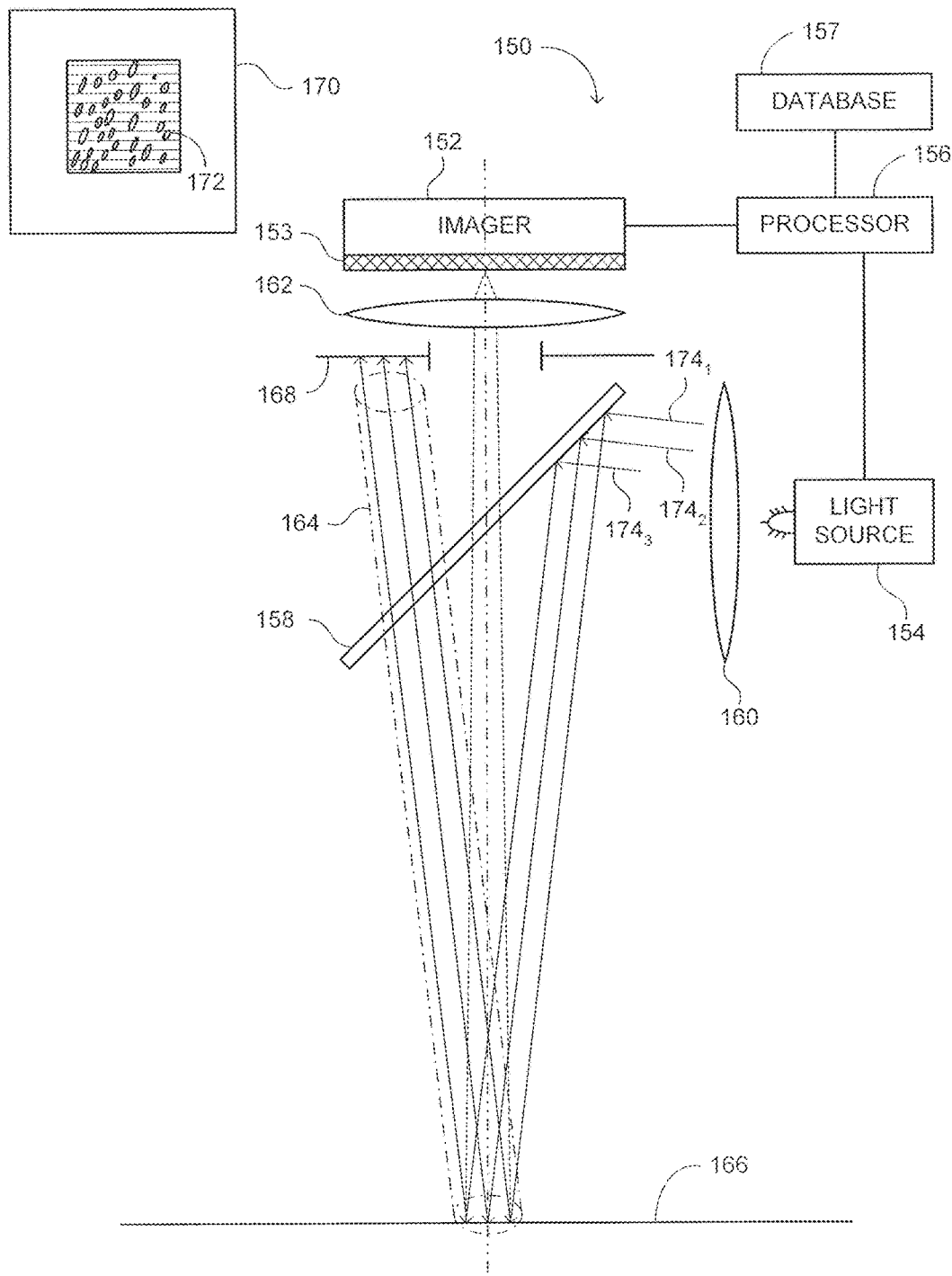
FIGS. 2A and 2B are schematic illustrations of a system for detecting the authenticity of an object, constructed and operative in accordance with another embodiment of the disclosed technique.
Figure 2B:
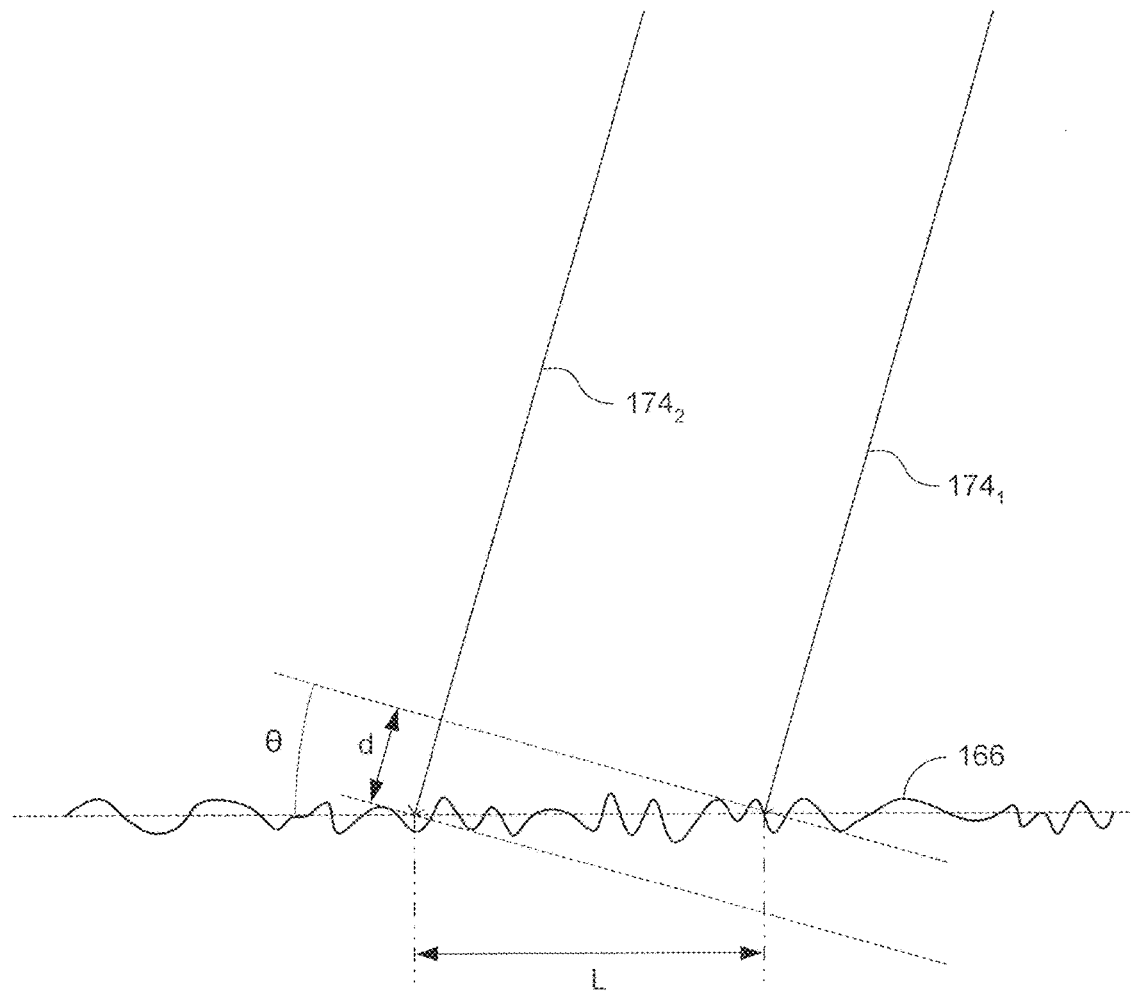

Reference is now made to FIGS. 2A and 2B which are schematic illustrations of a system, generally referenced 150, for detecting the authenticity of an object, constructed and operative in accordance with another embodiment of the disclosed technique. System 150 is employed in a use module when a user seeks to verify or determine the authenticity of an object. With reference to FIG. 2A, system 150 includes an imager 152, a light source 154, a processor 156, a database 157. Imager 152 includes an imaging sensor 153. System 150 includes light source optics 160 and imaging optics 162. Optionally, system 150 further includes a beamsplitter 158 and an aperture 168. Processor 156 is coupled with imager 152, with light source 154 and with database 157. Light source optics 160 is optically coupled with light source 154 and with beamsplitter 158. Imaging optics 162 is optically coupled with imager 152 and with beamsplitter 158. Light source optics 160 is either collimating optics or telecentric optics. In FIG. 2A, aperture 168 is depicted as being located between beamsplitter 168 and imaging optics 162. However, aperture 168 may alternatively be located between imaging optics 162 and imager 152.

Light source 154, which is similar to light source 104 (FIG. 1), directs light through light source optics 160 toward beamsplitter 158. Light source optics 160 collimates the light passing therethrough, such that collimated light, such as light rays $174_1$, $174_2$ and $174_3$ are directed toward beamsplitter 158. Beamsplitter 158 deflects the light from light source 154 toward the surface 166 of an authentication region of an object. The light impinges on surface 166 at an oblique angle relative to the normal of the object plane at the authentication region. The oblique impingement angle of the light is achieved either by rotating light source 154, or beamsplitter 158 or light source optics 160 to the desired angle.

The light impinges one surface 166. A portion of the light is scattered and another portion is reflected (i.e., specularly reflected). The specularly reflected light defines a specular reflection region, through which specular reflected light propagates, such as specular reflection region 164. In other words specular reflection region 164 relates to the region in space defined by the beam of specularly reflected light.

As mentioned above, the region defined by imaging sensor 153 and specular reflection region 164 are mutually exclusive in space. According to one example, aperture 168 blocks the specular reflected light from impinging on imaging sensor 153. Alternatively, imager 152 is positioned such that specular reflection region 164 and the region defined by imaging sensor 103 do not overlap and the specular reflected light does not impinge on imaging sensor 103. Consequently, imager 152 acquires an image of surface 166 resulting only from light scattered from surface 166.

Processor 156 determines the correspondence between the acquired and stored images similarly to as described above. Processor 156 identifies surface 166 as corresponding to an authentic object when the acquired image or images correspond to a stored image or images which are stored in database 157. Processor 156 identifies surface 166 as corresponding to a non-authentic object when the acquired image or images do not correspond to stored image or images.

With reference to FIG. 2B, collimated light rays, 174$_1$ and 174$_2$ impinging on a surface 166. The distance 'L', between the light rays 174$_1$ and 174$_2$, corresponds to the length of the area covered, on surface 166, by a single pixel. The distance 'd' corresponds to the difference between the wavefronts associated with each of light rays, 174$_1$ and 174$_2$ at surface 166. The value d should be smaller than the coherence length of the light ξ, (e.g., on the order of 1 um for a white light source). The angle θ, at which the light rays impinge on surface 166, the distance d and L are related according to the following:

$$\sin\theta = d/L \quad (1)$$

L depends on the actual pixel size (i.e., on the imaging sensor) and the magnification of the imaging optics as follows:

$$L = P/M \quad (2)$$

where P is the actual pixel size and M is the magnification of the imaging optics. According to the above, the light coherence length ξ should be larger than the distance d (i.e., ξ>d) and the maximum angle θ at which the light rays can impinge on surface 166, for a given pixel size and imaging optics magnification determined as follows:

$$\theta \le \sin^{-1}\frac{M\xi}{P} \quad (3)$$

For example, for an imager with a typical CMOS sensor where the pixel size is 5 micrometers (μm) (i.e., P=5 μm) and with magnification of 1 (i.e., M=1) then the maximum angle θ at which the light rays can impinge on surface 166 is 0.2 radians (i.e., θ≤0.2 radians). It is noted that when light source 154 is a coherent light source (e.g., a laser) the restriction over d does not apply. However, illuminating surface 166 at an oblique angle relative to the normal of the surface plane is still necessary.

The 'oblique illumination imaging' described hereinabove, results in an image 170, in which various image features 172, related to surface 166, can be identified in the acquired image. As mentioned above, these image features 172 are, for example, speckle pattern or surface irregularities such as scratches, cracks protrusions and the like. When the stored image or images are also acquired with 'oblique illumination imaging', these image features are also identified in the stored image or images and reduce the probability of false detection of a non-authentic object relative to relative to the probability of false detection when employing an image which does not include representations of the surface irregularities.

Figure 2C:
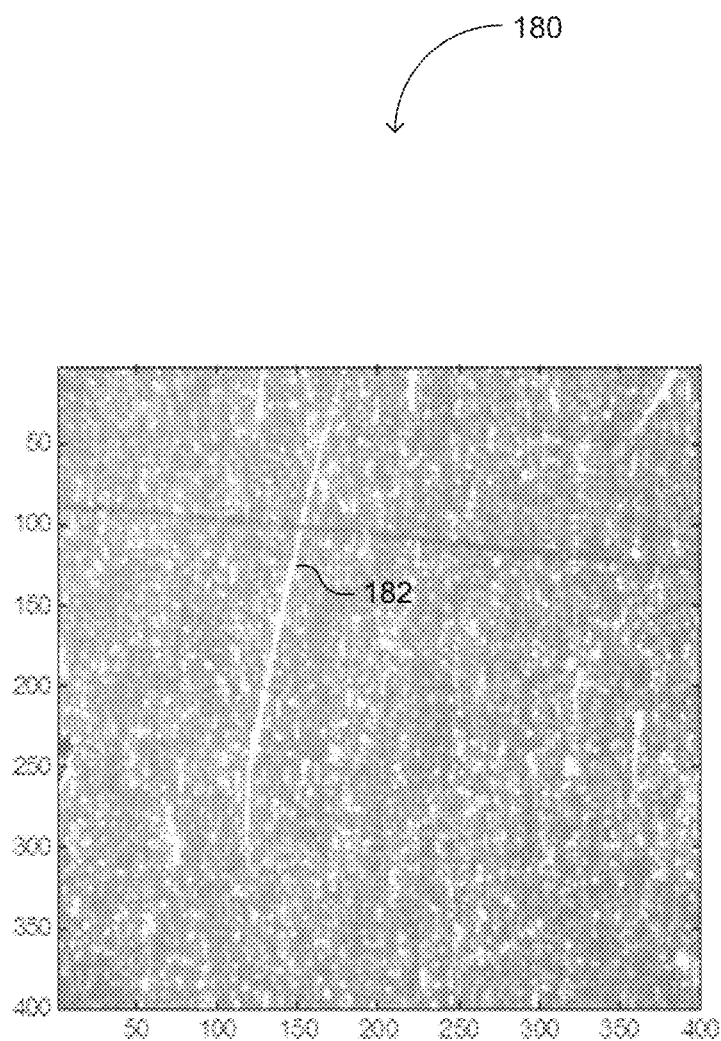
FIG. 2C is an exemplary illustration of an image acquired with 'oblique illumination imaging', in accordance with another embodiment of the disclosed technique.

Reference is now made to FIG. 2C, which is an exemplary illustration of an image, generally referenced 180, acquired with 'oblique illumination imaging', in accordance with another embodiment of the disclosed technique. The area of the authentication region observed in image 180 is approximately 5×5 millimeters. In acquired image 180 image features, such as a speckle pattern and scratch 182, are also identified in the image.

As mentioned above, the authentication region exhibits scattering characteristics, which depend on the wavelength of the light incident thereon. These scattering characteristics are related to the surface features and material characteristics of the authentication region, at the area observed by each pixel. The spectral response of the scattered light is also related to the structure of these surface features (e.g., slope, depth and the like). Therefore, an image based on the multi-spectral scattered light from the authentication region exhibits image features which are related to the surface features scattering phenomena, which are dependent on the wavelengths of the light incident on the imaging sensor. For example, the position and shape of the dark and bright areas in the speckle patterns can vary for different wavelengths and spectral schemes. Thus, illuminating the object with a multi-spectral light and imaging with a color or a multi-spectral imager increases the amount of information available for the system.

According to a further embodiment of the disclosed technique, the light emitted by the light source exhibits an emitted spectral scheme. The emitted spectral scheme includes at least two wavelength over at least two respective emitted spectral ranges. The emitted light impinges on the authentication region and scatters and reflects therefrom. At least a portion of the light scattered from the authentication region impinges on an imaging sensor of an imager. The imager acquires at least one focused image of the authentication region resulting from the scattered light, over the spectral response of the imager. The spectral response of the imager includes at least two acquired spectral ranges. Each acquired spectral range is associated with a corresponding spectral authentication image. The processor determines correspondence between at least one spectral authentication image, and a stored spectral authentication image which also correspond to the same spectral range of the imager, and determines the authenticity of the object accordingly. Employing at least two spectral authentication images corresponding to two respective spectral ranges reduces the probability of false detection relative to the probability of false detection when only a single image is employed.

Figure 3A:
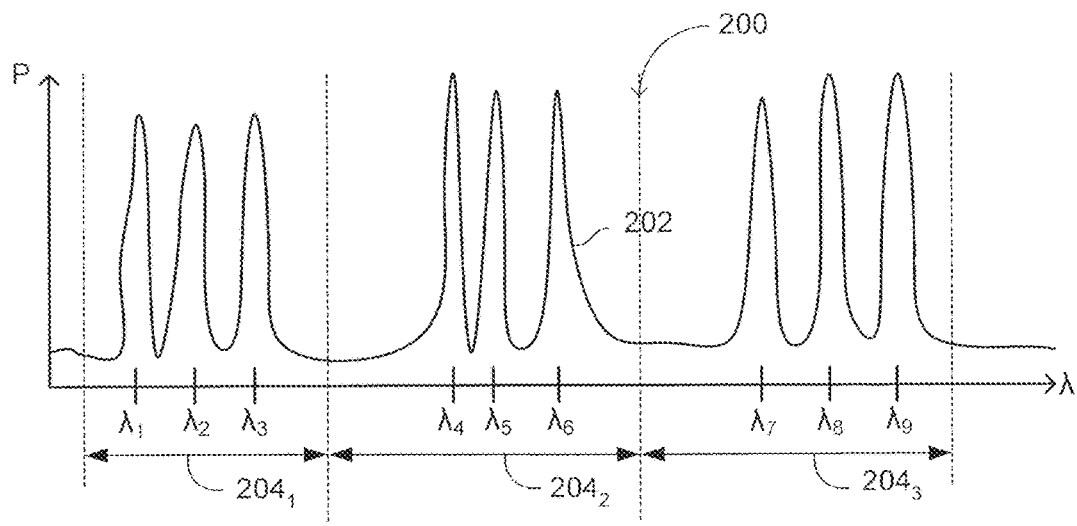
FIGS. 3A and 3B are schematic illustration of spectral diagrams in accordance with a further embodiment of the disclosed technique.
Figure 3B:
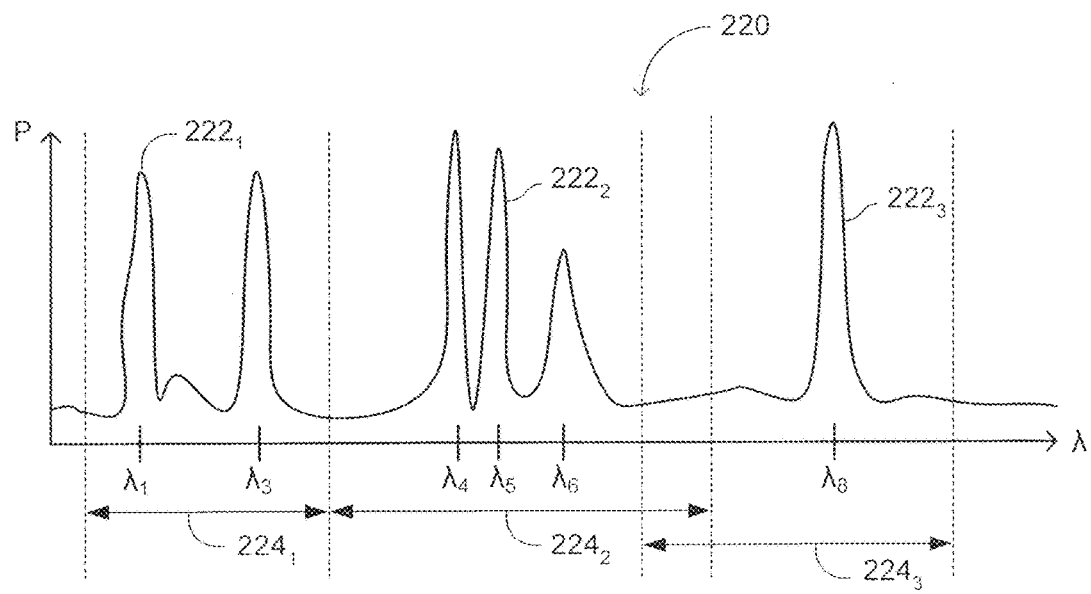

Reference is now made to FIGS. 3A and 3B, which are schematic illustration of spectral diagrams, generally referenced 200 and 220 respectively, in accordance with a further embodiment of the disclosed technique and referring back to FIG. 1. Light source 104 emits light via light source optics 110 toward beamsplitter 108. The emitted light exhibits an emitted spectral scheme. The term 'spectral scheme' herein relates to wavelengths composition (i.e., the wavelengths and their respective amplitudes) of the light. The emitted spectral scheme includes more than one wavelength over at least two respective emitted spectral ranges (e.g., wavelengths in the visible band, in the infrared band or the ultraviolet band or in a combination thereof, to which imager 102 is also sensitive). When light source 104 emits coherent light, the emitted spectral scheme includes at least two wavelengths over at least two respective emitted spectral ranges. When light source 104 emits non-coherent or partially coherent light, the emitted spectra scheme includes at least two spectral bands. Light source 104 may emit a combination of coherent and non-coherent or partially coherent light. With reference to FIG. 3A, spectral diagram 200 depicts an exemplary emitted spectral scheme 202.

Emitted spectral scheme 202 exhibits peaks at nine different wavelengths, $\lambda_1$, $\lambda_2$, $\lambda_3$, $\lambda_4$, $\lambda_5$, $\lambda_6$, $\lambda_7$, $\lambda_8$ and $\lambda_9$ over respective emitted spectral range $204_1$, $204_2$ and $204_3$. For example, emitted spectral range $204_1$, $204_2$ and $204_3$ may all be in the visible band. As a further example, emitted spectral range $204_1$ is in the infrared band, emitted spectral range $204_2$ is in the visible band and emitted spectral range $204_3$ is in the ultraviolet band. As another example, emitted spectral range $204_1$ is in the infrared band and emitted spectral ranges $204_2$ and $204_3$ are in the visible band. The emitted spectral scheme includes, for example, discrete wavelength as described herein. However, It is noted that, in general, the emitted spectral scheme may be continuous within the spectral band of interest, though not necessarily uniform. Furthermore, the emitted spectral scheme may be continuous in one emitted spectral range and discrete in another emitted spectral range. Beamsplitter 108 directs the light toward authentication region 116 of object 118.

The light impinges on the surface of authentication region 116 and scatters and reflects therefrom. The light scattered from each area observed by each pixel on the authentication region exhibits a respective scattered spectral scheme. In general, the amplitudes of the reflected spectral schemes depend on the surface features and material characteristics of authentication region 116.

A portion or the scattered light (i.e., the portion directed toward system 100) is directed via, beamsplitter 108 and imaging optics 112 toward imager 102. In other words, at least a portion of the light scattered from authentication region 116 impinges on imaging sensor 103. Imager 102 acquires at least one focused image or images (e.g., image 120) of authentication region 116. The acquired focused image or images of authentication region 116 at least includes a speckle pattern (i.e., a speckle pattern is identifiable in the image). The acquired image may include additional image features (e.g., scratches, cracks or protrusions). The spectral response of imager 102 includes at least two acquired spectral ranges. Each acquired spectral range is associated with a corresponding spectral authentication image. As a result of the wavelength dependency of the scattering diffraction and/or reflection of the light from the authentication region, each spectral authentication image may exhibit different image features related to surface features scattering phenomena. With reference to FIG. 3B, spectral diagram 220 depicts exemplary acquired spectral schemes $222_1$, $222_2$ and $222_3$, of the light impinging on a single pixel, each over a respective spectral range $224_1$, $224_2$ and $224_3$. The acquired spectral scheme can be different for each pixel. This acquired spectral scheme relates to the material characteristics and surface features of the area observed by the specific pixel. It is noted that the spectral ranges of the acquired spectral schemes may partially overlap. For example, spectral ranges $224_2$ and $224_3$ partially overlap with each other.

Processor 106 identifies from the acquired image, at least one spectral authentication image of authentication region 116 corresponding to a respective one of spectral ranges $224_1$, $224_2$ and $224_3$. For example, processor 106 employs acquired spectral ranges $224_1$ and $224_2$ and identifies the respective spectral authentication images corresponding thereto. Processor 106 then determines the correspondence between the identified spectral authentication image or images and stored spectral authentication image or images (stored in database 107), which also correspond to the same acquired spectral range. When the identified spectral authentication image or images corresponds to the stored spectral authentication image or images, processor 106 identifies object 118 as authentic. When the identified spectral authentication image or images do not correspond to the stored spectral authentication image or images, processor 106 identifies object 118 as non-authentic. In general, the combinations of the spectral ranges employed may be predetermined, randomly or cyclically determined (i.e., from a group of spectral ranges combinations).

Following is an example of determining the authenticity of an object employing the color imaging technique and still referring to FIG. 1. Light source 104 is, for example a LED emitting light at a known spectral scheme. Light source 104 may also be, a standard illuminant (e.g., a CIE D65 illuminant, a CIE D50 illuminant, a CIE F series illuminant and the like), which emits light with a known emitted spectral scheme toward authentication region 116 of object 118. The light impinges on authentication region 116. However, not all of the light that impinges on authentication region is scattered therefrom. Some of the wavelength may be absorbed or partially absorbed by object 118. As mentioned above, authentication region 116 scatters a portion of the light impinging thereof toward imager 102. Imager 102 includes an imaging sensor, such as imaging sensor 103, capable of acquiring, for example, a color image in the RGB color space. Accordingly, imager 102 acquires an RGB image over three acquired spectral ranges, the red acquired spectral range, the green acquired spectral range and the blue acquired spectral range. Also, each one of acquired spectral range is associated with a corresponding spectral authentication image. In other words the acquired image is comprised of the spectral authentication images. Thus, when the acquired image is an RGB image, there are three spectral authentication images corresponding to each of the red, green and blue acquired spectral ranges. Each spectral authentication image includes image features related to surface scattering phenomena of authentication region 116. In other words, the image features related to surface features scattering phenomena are identifiable in the image.

Processor 106 employs at least one spectral authentication image. Processor 106 determines if this spectral authentication image or images correspond to stored spectral authentication images, which also correspond to the same spectral range or ranges. For example, processor 106 selects the blue and red spectral ranges and identifies the spectral authentication images corresponding thereto. Processor 106 determines the correspondence between the identified spectral authentication image corresponding to the blue acquired spectral range, with a stored spectral authentication image also corresponding to the blue acquired spectral range, which is stored in database 107. Processor 106 further determines the correspondence between the identified spectral authentication image corresponding to the red acquired spectral range with a stored spectral authentication image also corresponding to the red acquired spectral range, which is also stored in database 107. When the processor 106 determines that the identified spectral authentication images, corresponding to both the red and the blue spectral ranges, correspond to the stored spectral authentication images, corresponding to the red and the blue spectral ranges, processor 106 identifies object 118 as authentic. Otherwise, processor 106 identifies object 118 as non-authentic.

Figure 4A:
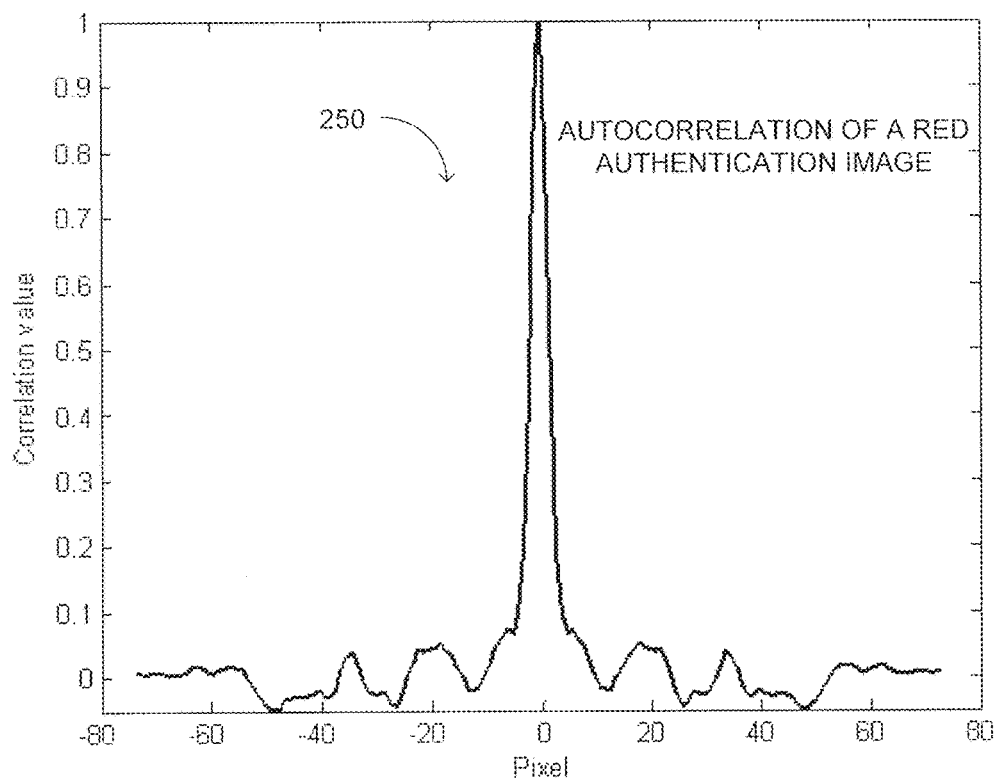
FIGS. 4A and 4B are exemplary illustrations of diagrams in accordance with another embodiment of the disclosed technique.
Figure 4B:
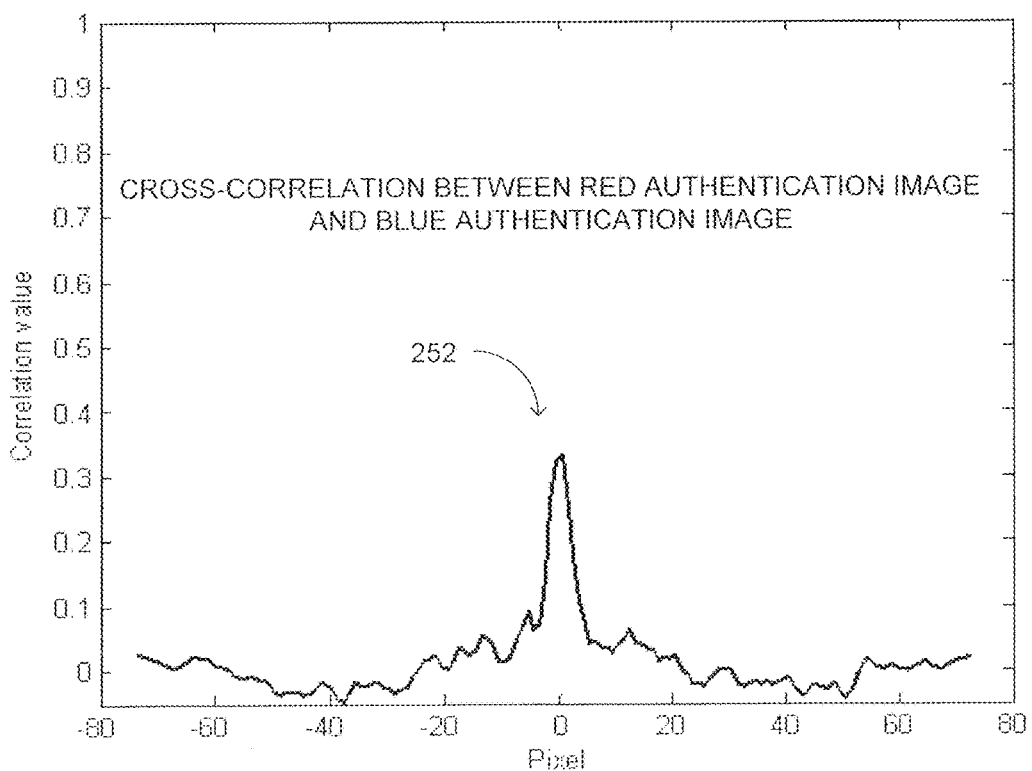

Continuing with the above example relating to an RGB image, Reference is now made to FIGS. 4A and 4B, which are exemplary illustrations of diagrams, generally referenced 250 and 252 exhibiting autocorrelation and cross-correlation for authentication in accordance with another embodiment of the disclosed technique. Diagrams 250 and 252 illustrate the advantages of the color imaging technique.

Diagram 250 in FIG. 4A depicts the result of the autocorrelation of a red spectral authentication image. As can be seen the peak value of this autocorrelation of the red spectral authentication image is substantially one. Diagram 252 in FIG. 4B depicts the result of the cross-correlation between the red spectral authentication image and the blue spectral authentication image. As can be seen in FIG. 4B, the maximum value of the cross-correlation value between the red spectral authentication image and the blue spectral authentication image is significantly lower than one. This implies that, although the two images may share some commonalities, the information contained in these two images is different (e.g., the speckle patterns in these images may be different). As such, in general, when processor 106 employs at least two spectral authentication images corresponding to two different spectral ranges, the probability of false-detection of a non-authentic object is reduced relative to a system which employs a single spectral authentication image.

It is noted that the above described 'oblique illumination imaging' technique and 'color imaging' technique may be employed conjointly. For example, referring back to FIG. 2A, the light emitted light source 154 may be a multi-chromatic light (i.e., exhibiting an emitted spectral scheme which includes at least two wavelengths over at least two respective emitted spectral ranges) and the spectral response of imager 152 includes at least two acquired spectral ranges where each acquired spectral range is associated with a corresponding spectral authentication image as described above. As a further example, referring back to FIG. 1, light source optics 110 are either collimating optics or telecentric optics and the light emitted from light source 104 is directed toward authentication region 116 such that the light impinges on authentication region 116 at an oblique angle relative to the normal to the object plane at the authentication region. The oblique illumination is achieved either by rotating light source 104, or beamsplitter 108 or light source optics 110 to the desired angle and position. When the 'oblique illumination imaging' technique and 'color imaging' technique are employed conjointly, the probability of false detection of a non-authentic object is reduced relative to the probability of false detection when only one of these techniques is employed. As mentioned above, employing the oblique illumination allows authentication of objects with reflecting or partially reflecting surfaces. It is further noted that in an object authentication system according to any one of the embodiments of the disclosed technique, the magnification is smaller than one (i.e., the system is not a microscopic imaging system). Thus, the positioning to the system relative to the authentication region is simplified relative to a system with a magnification larger than 1.

It is noted that when employing the imaging technique with normal illumination and normal imaging (i.e., not with the oblique illumination imaging technique described herein above), the mean pixel values of the acquired images of partially reflecting surfaces and specularly reflecting surfaces may be larger than pixel values related to the image features related to surface features scattering phenomena (e.g., speckle pattern or scratches). Thus, the image features related to the surface features scattering phenomena shall not necessarily be identifiable in the image (i.e., since the pixel values of the image features relating to the surface features scattering phenomena shall be smaller than the Least Significant Bit (LSB) of the pixel value and thus un-identifiable in the acquired image). Attempting to increase the intensity of the light, shall cause saturation in at least some of the pixels (i.e., due to specular reflection).

Figure 5:
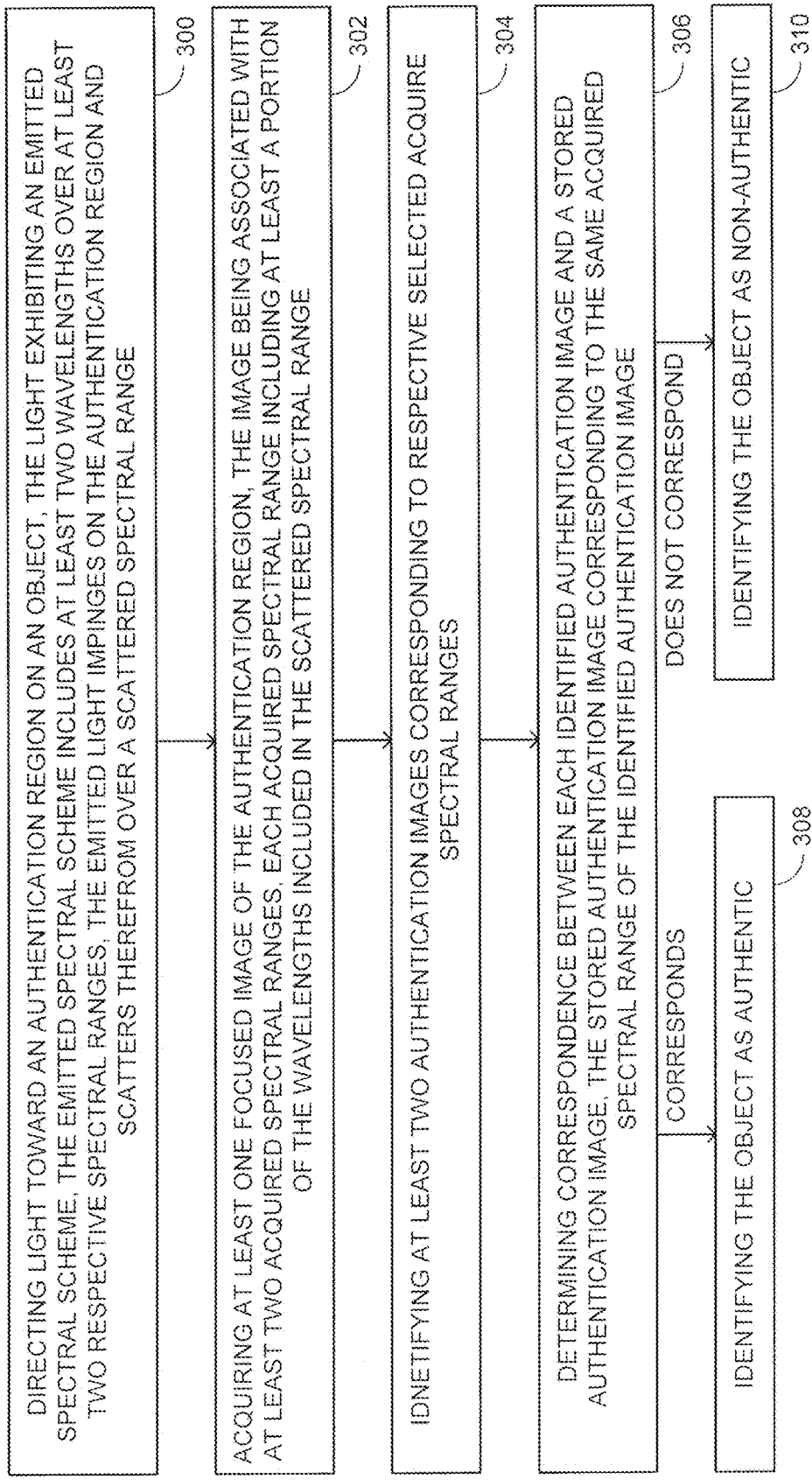
FIG. 5, is a schematic illustration of a method for determining the authenticity of an object, operative in accordance with a further embodiment of the disclosed technique.

Reference is now made to FIG. 5, which is a schematic illustration of a method for determining the authenticity of an object, operative in accordance with a further embodiment of the disclosed technique. In procedure 300, light is directed toward an authentication region on an object. The light exhibits an emitted spectral scheme. The emitted spectral scheme includes at least two wavelengths over at least two respective spectral ranges. The light impinges on the surface of the authentication region and scatters and reflects therefrom. The light scattered from each area observed by each pixel on the authentication region exhibits a respective scattered spectral scheme. Optionally, the light impinges on the authentication region at an oblique angle relative to the normal of the object plane. With reference to FIG. 1, light source 104 directs light toward authentication region 116 on object 118.

In procedure 302, At least one focused image of the authentication region is acquired. The image is associated with at least two acquired spectral ranges. Each acquired spectral range including at least a portion of the wavelengths included in the scattered spectral range. With reference to FIG. 1, imager 102 acquires at least one focused image of authentication region 116. With reference to FIG. 3C, the image is associated with at least two of acquired spectral ranges $224_1$, $224_2$ and $224_3$.

In procedure 304, at least two spectral authentication images corresponding to respective acquire spectral ranges are identified. The respective acquired spectral ranges may be, for example, predetermined, randomly or cyclically determined. With reference to FIG. 1, processor 106 identifies at least two spectral authentication images corresponding to respective acquire spectral ranges.

In procedure 306, the correspondence between each identified authentication image and a stored spectral authentication image is determined. The stored spectral authentication image corresponds to the same acquired spectral range of the identified spectral authentication image. With reference to FIG. 1, processor 106 determines the correspondence between each identified spectral authentication image and a stored spectral authentication image. When the identified and stored spectral authentication images, or the parts thereof, correspond to each other, the method proceeds to procedure 308. When the identified and stored spectral authentication images, or the parts thereof, do not correspond to each other, the method proceeds to procedure 310.

In procedure 308, the object is identified as authentic. With reference to FIG. 1, processor 106 identifies the object as authentic when the identified and stored spectral authentication images, or the parts thereof, correspond to each other.

In procedure 310, the object is identified as non-authentic. With reference to FIG. 1, processor 106 identifies the object as non-authentic when the identified and stored spectral authentication images, or the parts thereof, do not correspond to each other.

Authentication region 116 may exhibit predetermined scattering and reflection characteristics. Thus, when light exhibiting a selected emitted spectral scheme impinges on authentication region 116, the acquired spectral scheme of a group of pixels in an acquired image shall be the average scattered spectral schemes of area observed by the pixels in the group. Accordingly, spatial speckle information is lost, but the mean reflective properties of the surface can be determined. As mentioned above, imager 102 acquires a focused image of authentication region 118. Processor 106 determines, for example, the mean color values of a group of pixels in the acquired image, the color values being determined in a corresponding color space. The resulting averaged image has lower resolution and exhibits a color pattern (i.e., the color pattern may be uniform). The information relating to the mean color value contributes additional information relating to the object. Thus, the mean color value of a group of pixels may be employed as an additional parameter for determining the authenticity of an object (i.e., either independently or in conjunction with other parameters). Processor 106 compares the mean color values to those in images saved in the database. The lower resolution image can also be employed for identifying object coded identifiers (e.g., bar code) as further explained below.

As mentioned above, imager 102 acquires a focused image of authentication region 116. Since the acquired images (i.e., which are also focused) are compared with stored images, the surface features included in the stored and identified spectral authentication images should be substantially the same. However, the conditions during the acquisition of acquired image and the acquisition of the stored images, might differ. These different conditions relate, for example, to the defocus during the acquisition and the lateral position of the authentication region relative to the optical axis of the system. Since the surface features of the authentication region scatter the light impinging thereon and has a diffractive effect, the image features related to surface features scattering phenomena created at the sensor plane of imager 102 vary with the change in the relative lateral position between light source 104, object 118 and imager 102 and with the change in focal plane of the imaging optics (i.e., defocusing and variations in the image magnification as well).

Figure 6A:
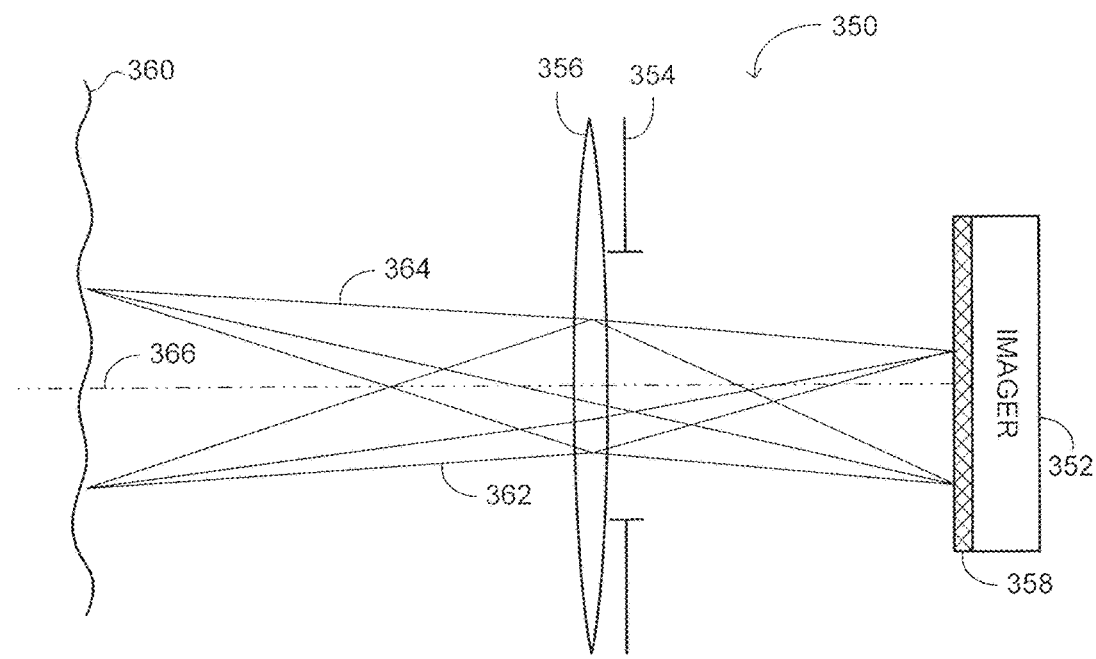
FIG. 6A is a schematic illustration of an image acquisition system employing conventional optics.
Figure 6B:
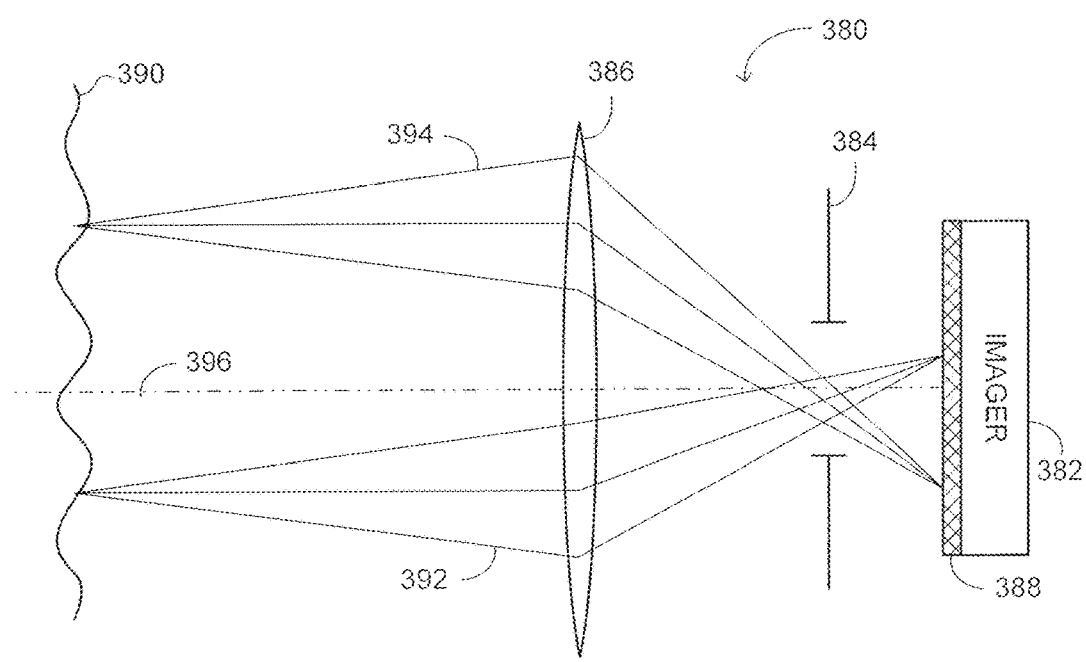
FIG. 6B is a schematic illustration of an image acquisition system employing telecentric optics, constructed and operative in accordance with another embodiment of the disclosed technique.

In order to desensitize the images to relative motion between system 100 and object 118 to defocusing and to variation in lateral position, telecentric optics may be employed in imaging optics 112. Reference is now made to FIGS. 6A and 6B. FIG. 6A is a schematic illustration of an image acquisition system, generally referenced 350, employing conventional optics. FIG. 6B is a schematic illustration of an image acquisition system, generally referenced 380, employing telecentric optics, constructed and operative in accordance with another embodiment of the disclosed technique. With reference to FIG. 6A, system 350 includes an imager 352, an aperture 354 and imaging optics 356. Imager 352 includes an imaging sensor 358. Aperture 354 is optically coupled with imaging sensor 358 and with imaging optics 356. When conventional optics is employed, system 350 exhibits an angular fields of view. Accordingly, cones such as cones 362 and 364, representing the path of the light impinging each pixel in imaging sensor 358, exhibit different orientations. In other words, the light gathered by each pixel in imaging sensor 358 exhibits a different cone orientation. Consequently, when the distance between imaging optics 356 and the object surface 360 increases, the magnification of the object decreases (i.e., similar to human vision). This change in magnification results in an effect, known as perspective error, which limits the ability to make precise measurements relating to the object, as the relative position between the object and imaging optics 356 changes along the optical axis 366 of system 350 (i.e., even when remaining within the depth of field). Collecting light with different cones exhibiting different orientations, causes variation in the image features when changes with the relative position between the object and imaging optics 356 occur.

Telecentric optics alleviates the perspective error characteristic of conventional optics. Thus the image features remain substantially similar with changes in the relative position between the object and imaging optics. With reference to FIG. 6B, system 380 includes an imager 382, an aperture 384 and imaging optics 386. Imager 382 includes an imaging sensor 388. Aperture 384 is optically coupled with imaging sensor 388 and with imaging optics 386. At any distance from imaging optics 386, system 380 shall always exhibit the same field of view. Moreover, cones such as cones 392 and 394, representing the path of the light impinging each pixel in imaging sensor 388 exhibit similar orientations. In other words, all the pixels in imaging sensor 388 gather light from cones, such as cones 392 and 394 that exhibit similar orientations. Therefore, imaging optics shall collect light exhibiting similar light cones, for all pixels, independent of the relative position between the object and imaging optics 384 (i.e., either the lateral position or the position along the optical axis 396 or both). Consequently image features remain substantially similar irrespective of changes in the relative position between the object and imaging optics 356.

Figure 6C:
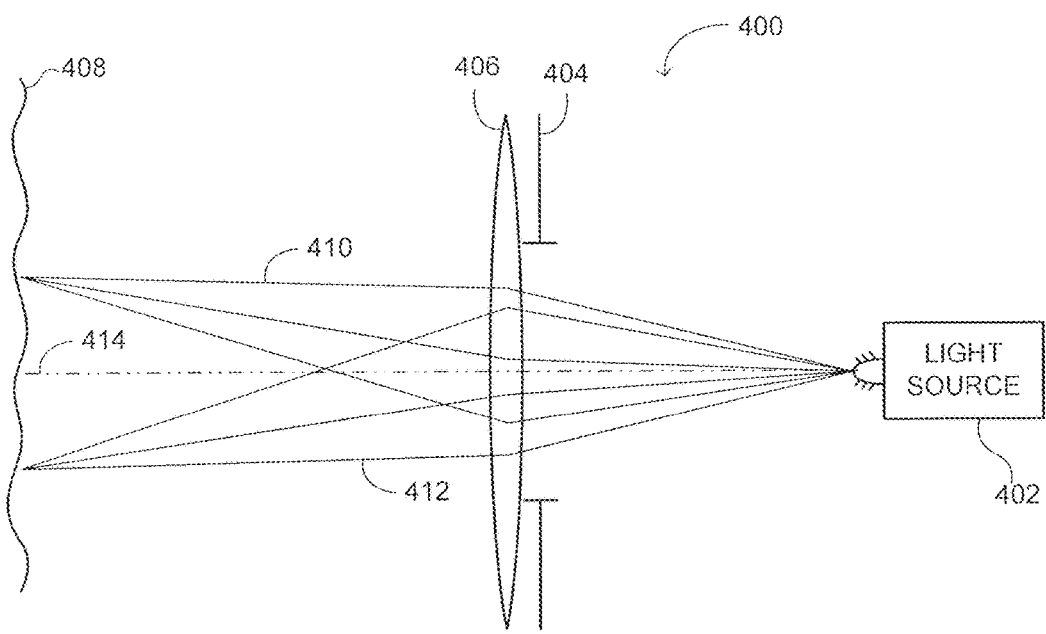
FIG. 6C is a schematic illustration of an illumination system, employing conventional optics.
Figure 6D:
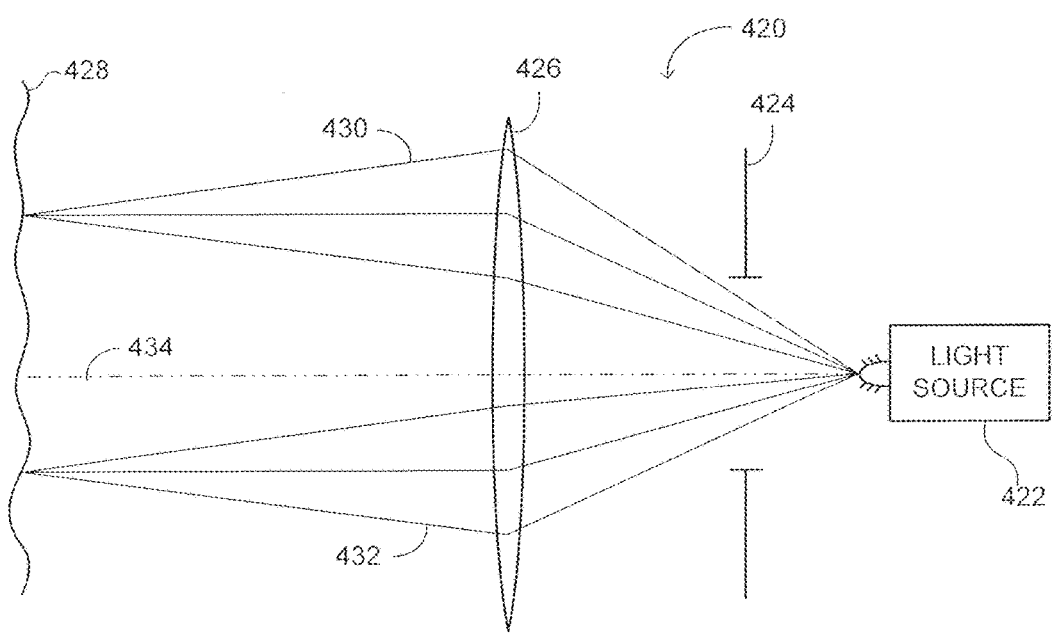
FIG. 6D is a schematic illustration of an illumination system employing telecentric optics, constructed and operative in accordance with a further embodiment of the disclosed technique.

Additionally, the light source optics may also be telecentric. Reference is now made to FIGS. 6C and 6D. FIG. 6C is a schematic illustration of an illumination system, generally referenced 400, employing conventional optics. FIG. 6D is a schematic illustration of an illumination system, generally referenced 420, employing telecentric optics constructed and operative in accordance with a further embodiment of the disclosed technique. With reference to FIG. 6C, illumination system 400 includes a light source 402, an aperture 404 and light source optics 406. Aperture 404 is optically coupled with light source 402 and with light source optics 406. The image of the surface features is sensitive to the orientation of the illumination cones such as cones 410 and 412. Thus, changes in the relative position between the object 408 and light source optics 406 (i.e., either the lateral position or the position along the optical axis 414 or both), results in different images for each relative position. Telecentric illumination optics may alleviate these phenomena. With reference to FIG. 6D, illumination system 420 includes a light source 422, an aperture 424 and light source optics 426. Aperture 424 is optically coupled with light source 422 and with light source optics 426. Light source optics is telecentric optics. Telecentric light source optics 426 results in a light beams impinging on surface 428 which exhibit similar cones such as cones 430 and 432, with similar divergence and orientation for each object position. Alternatively, the light source optics 426 may be collimating optics, in which all the light ray (i.e., not only the principle rays) are directed toward object 428 are parallel or diverging at the angles that small enough to keep on imaging independent to lateral translation.

Figure 6E:
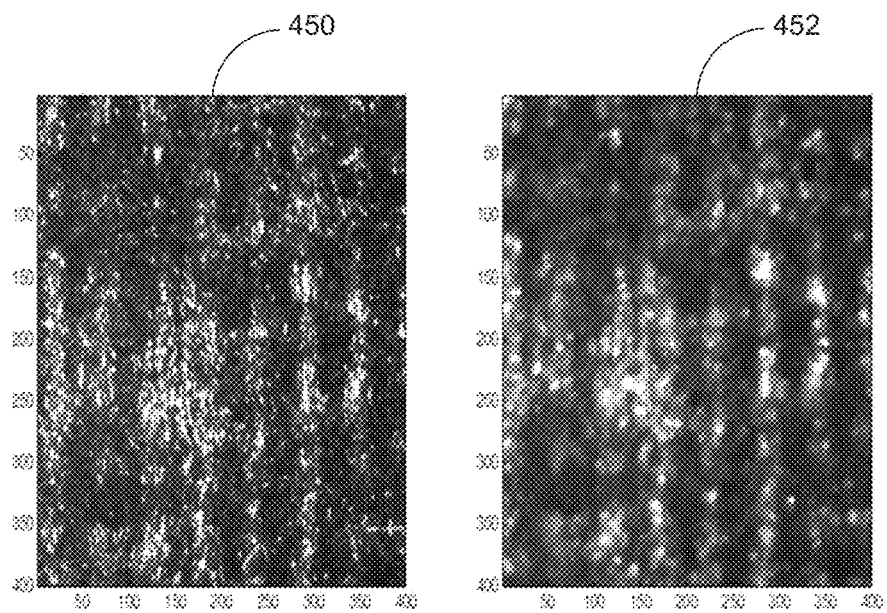
FIGS. 6E and 6F are schematic illustrations of images in accordance with another embodiment of the disclosed technique.
Figure 6F:
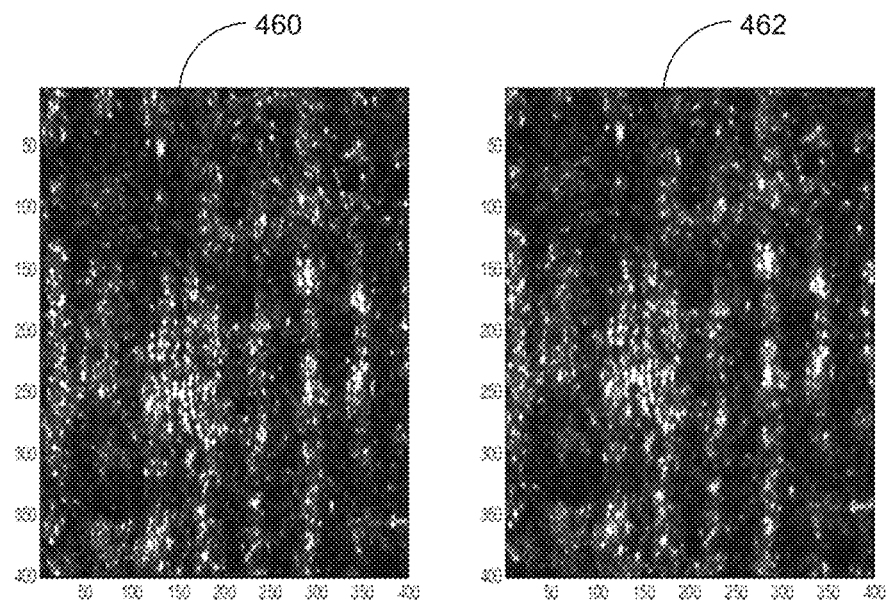

To illustrate the effect of telecentric optics, reference is now made to FIGS. 6E and 6F. FIG. 6E is a schematic illustration of two exemplary images 450 and 452 and FIG. 6F is a schematic illustration of two exemplary images 460 and 462, all in accordance with another embodiment of the disclosed technique. Images 450, 452, 460 and 462 were acquired during an experiment employing a system constructed according to the disclosed technique. The area of authentication region observed in images 450, 452, 460 and 462 is approximately 5×5 millimeters. With reference to FIG. 6E, images 450 and 452 depict images of a textile object, where the light source is collimated, the f-number is low and "regular" imaging optics is employed. However, image 450 is a focused image while image 452 is a defocused image of the textile object. As seen in FIG. 6E, the speckle pattern in FIG. 452 substantially changed relative to speckle pattern in imager 450. With reference to FIG. 6F, images 460 and 460 depict images of the textile object, where the light source is collimated, the f-number is high and "telecentric" imaging optics is employed. However, image 460 is a focused image while image 462 is a defocused image of the textile object. As seen in FIG. 6F, the speckle pattern in FIG. 462 did not substantially changed relative to speckle pattern in imager 460. It should be noted that the f-number of image 460 is higher than the f-number of image 450. Conventional imaging, as depicted in FIG. 6A, and corresponding image 450 in FIG. 6E, may cause changes in magnification, vignetting and defocusing.

As mentioned above, authentication region 116 may exhibit predetermined reflectance characteristics. Thus, when light exhibiting a selected emitted spectral scheme impinges on authentication region 116, authentication region 116 shall reflect a known reflected spectral scheme. Nevertheless, background light or light from authentication region 116 that underwent multiple scattering from within the object, loses the polarization state and the coherence length thereof, thus introducing additional noise to the image of authentication region 116. To avoid the reduction in the Signal to Noise Ratio (SNR) and in the dynamic range of the imager caused by background and multiple scattered light, parallel polarizers can be employed. In other words, the light emitted by light source 104 and the light impinging on the imaging sensor are polarized in the same predetermined direction, for example, with polarizers. Thus, intensity of the light that does not exhibit polarization in that same predetermined direction shall be reduced.

To further reduce the probability of false detection, imager 102 may acquire an image of a barcode, a Quick Response (QR) code or any other object coded identifier (e.g., serial number) of the object or batch of objects, which is appended to object 118. The image of the object coded identifier may be the same acquired image of the authentication region. Alternatively, the image of the coded identifier may be a different image (i.e., acquired separately) but linked to the image of the authentication region. Processor 106 then identifiers the object coded identifier and compares to coded identifier to coded identifiers stored in database 107. Processor 106 employs the object coded identifier as a parameter in determining the authenticity of the object. Furthermore, once the object unique identifier is identified, this unique identifier may be employed as a pointer of the stored image used for authenticating the object and that should have the same object unique identifier.

In general, when detecting the authenticity of an object employing a system according to the disclosed technique, the image features corresponding to the scattering phenomena may change with the relative orientation between the system and the authentication region (e.g., due to directionality of the light impinging on the authentication region). Therefore, the object may include a symbol that indicates a recommended relative orientation between the authentication system and the authentication region. The indicated relative orientation is similar to a relative orientation at which the stored image was acquired (i.e., there can be more than one relative orientation at which the stored image was acquired).

It is noted that a system according to the disclosed technique, may be located on a portable device. For example, the system may be incorporated in a smartphone or in a tablet computer. As such, the imager, the light source, the light source optics and the imaging may be incorporated in the portable device and the Imager and the light source shall be coupled to the processor of the portable device. For example, the system may be attached to a portable device (e.g., with the aid of a magnet or suction cups). As a further example, the image, the light source and the processor of the portable may be employed however, additional optics should be employed (e.g., attached to the portable device), especially when the oblique illumination technique is employed. Alternatively, the system may be a standalone system with a wireless communication link such as WiFi or Bluetooth or a wired communication link. As a further example, the system may be attached to a portable device (e.g., with the aid of a magnet or suction cups). In addition, the Database may be located on the portable device or at a remote location. When the database is located at a remote location (e.g., at the manufacturer), the processor may be coupled with the database via a communication network (e.g., internet).

When a system according to the disclosed technique is located on a portable device the portable device may move during the acquisition of the image, resulting in the blurring of the image. Therefore, the system may include motion sensor (e.g., accelerometers, gyro-sensors) which detect the motion of the system. Alternatively, the motion of the system may be detected by cross-correlating two successive images. If the cross-correlation between the images is less the one pixel, than the system is determined to be stationary. The system acquires an image only when the sensor indicates that the system is substantially stationary.

It is noted that in general, the distance between system and the object during the acquisition of the images (i.e., either the stored image or the acquired image employed for authentication) should be substantially the same and constant during the acquisition. To that end, a physical spacer exhibiting a predetermined width is employed, where the system is positioned at one end of the space and the object is positioned at the other end. The physical space may be incorporated into the housing of the system. The spacer may exhibit the form of a tube, thus reducing the effects of background light on the acquired image.

The disclosed technique, described above in conjunction with FIGS. 1A-1D, and 2 are related to an authentication region which reflects the light impinging thereon. However, the disclosed technique is also applicable to authentication regions which transmit the light impinging thereon. To that end, the light source and the imager should be located on opposite sides of the authentication region such that the light emitted by the light source passes through the authentication region and impinges on the imager. Also instead of a reflected spectral scheme the light emerging from the authentication region shall exhibit a transmitted spectral scheme.

In general, the disclosed technique may be employed by potential customers interested in purchasing an object. When the system is employed with a portable device which can identify the location of the user (e.g., Global Positioning System—GPS or WiFi), the query is sent to database 107 with the acquired focused speckled image, may include the location of the user (e.g., the address of the user, the coordinates of the user). The response from the database may include an indication of the location of the user corresponds to a valid vendor of the object or even a rating of the vendor.

Additionally, to avoid misuse of the system (e.g., user sending spam images to the database), a query is sent to the database only if a query identifier is provided. This query identifier may be a code provided by the vendor, a vendor identifier (e.g., the name of the store) or the object unique identifier. The vendor identifier may be identifiable in the acquired image. For example, a card including the vendor identifier is placed near the authentication region. The processor determines the query identifier and determines if the query identifier corresponds to a valid vendor or product. Only when the query identifier corresponds to a valid vendor or product, the processor determines the authenticity of the object.

The system according to the disclosed technique may be employed in various applications such in games. For example, in mixed reality games, real object may be identified according to the speckled image thereof and identified as a part of the game. As a further example, a square in a chess game may be uniquely identified according to the speckled image thereof. As an additional example, the system according to the disclosed technique may be employed to authenticate cards in a card game thus reducing the probability of additional cards being introduced to the game. As another example, in modular structures, a system according to the disclosed technique may be employed for detecting congruent modules which are to be fitted one with the other. To that end, for example, the system identifies a first module according to an acquired image thereof. Thereafter, the system identifies from a plurality of other modules, a second module congruent with the first module. Thus, a user can determine with a degree of certainty that two modules are congruent.

Figure 7A:
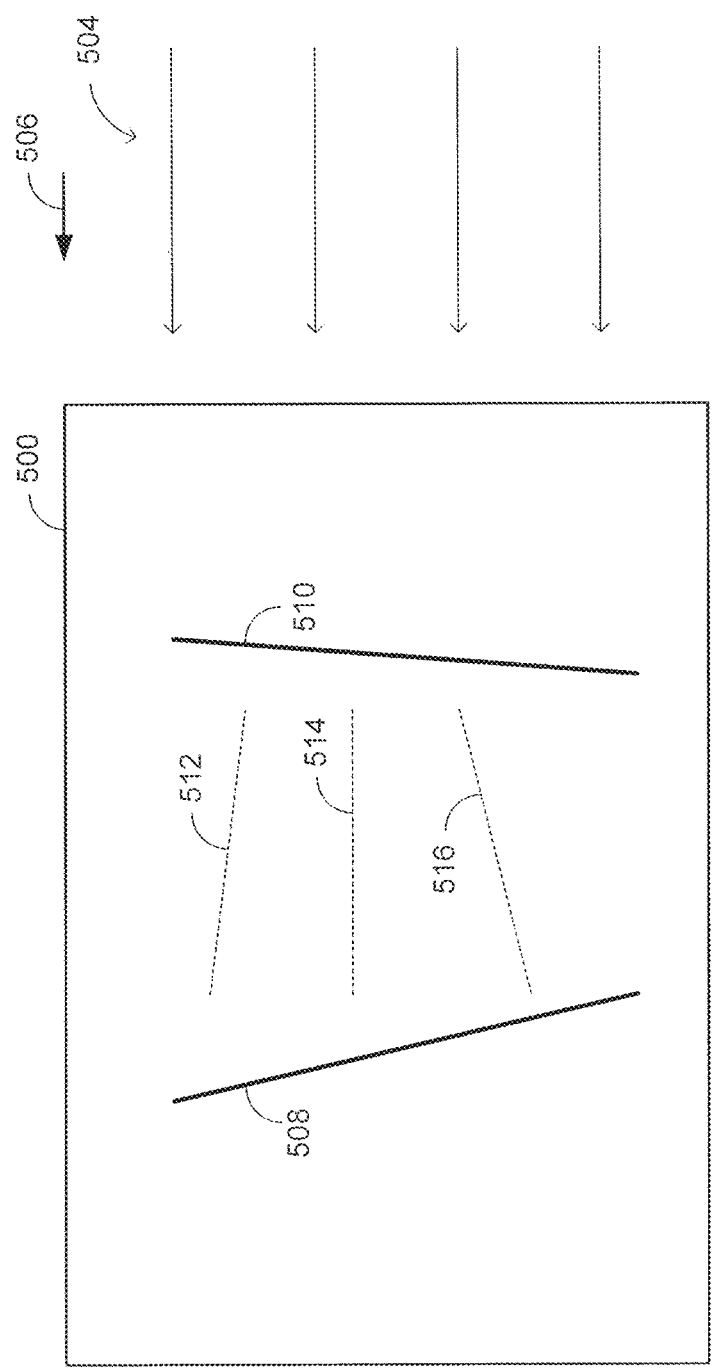
FIGS. 7A and 7B are schematic illustrations of images including features corresponding to the scattering phenomena in accordance with another embodiment of the disclosed technique.
Figure 7B:
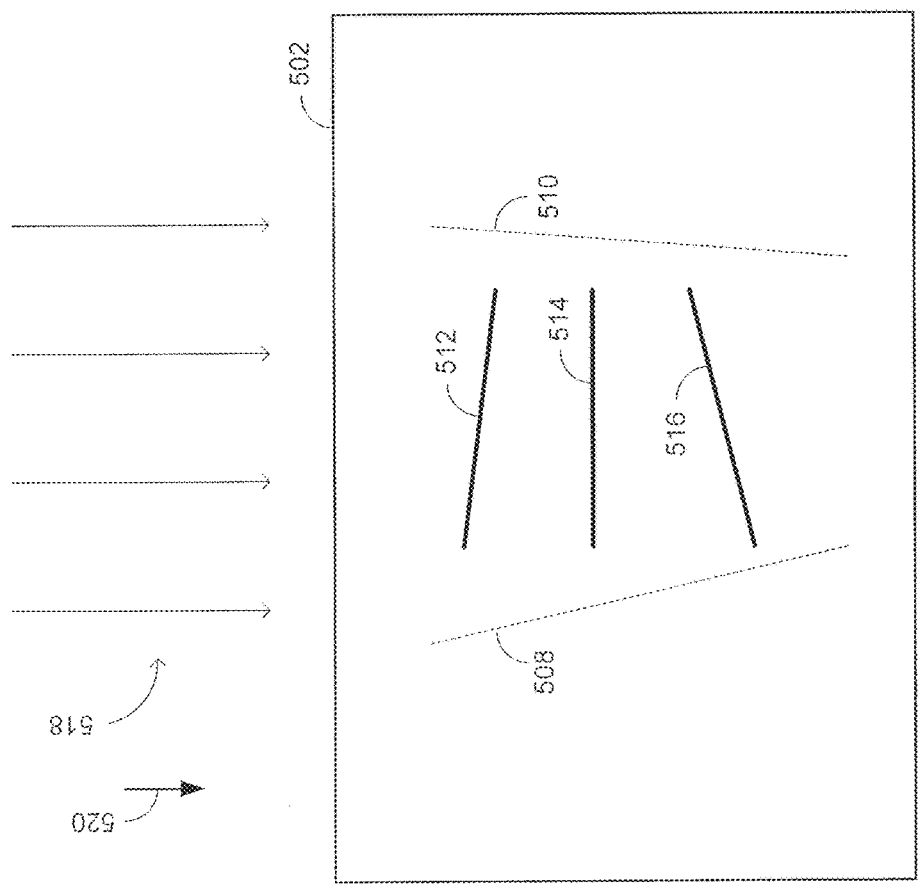
Figures 7C, 7D:
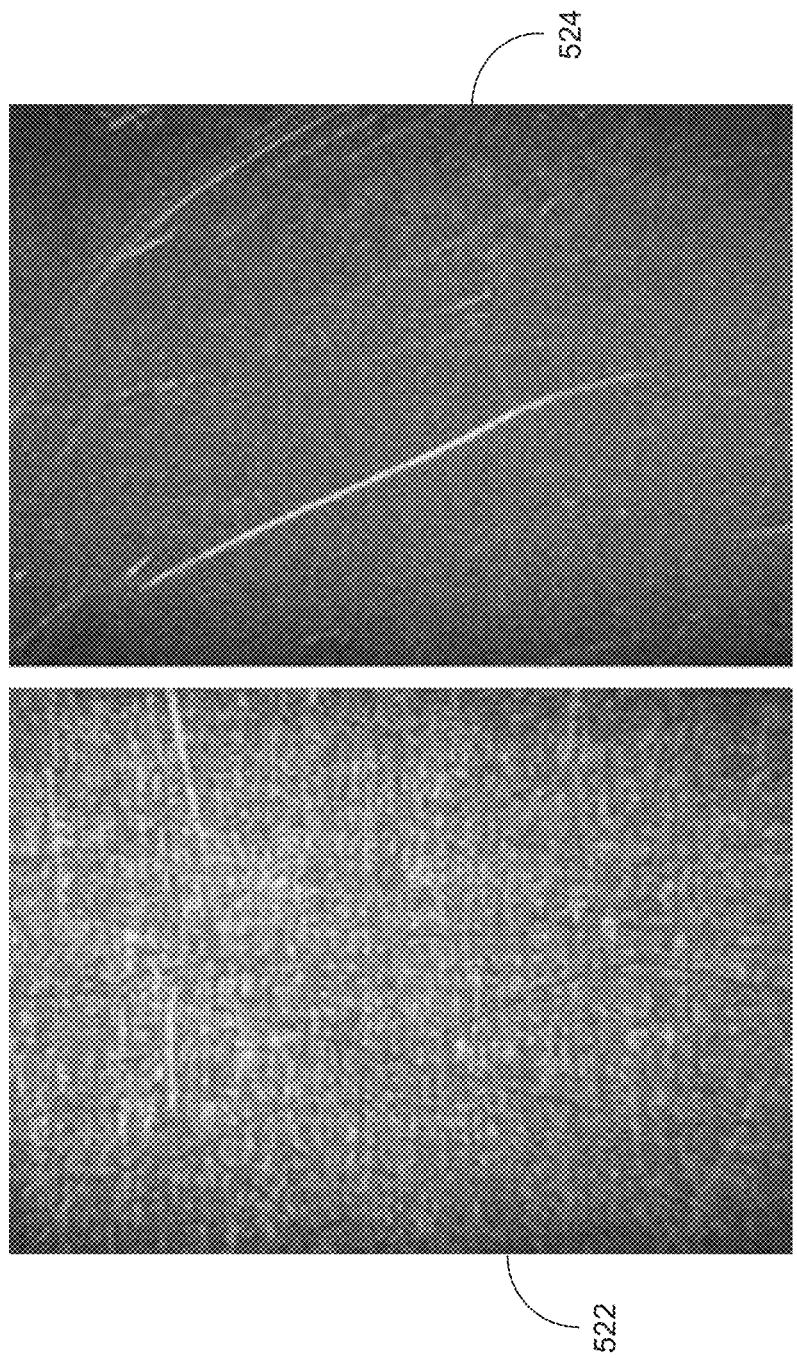
FIGS. 7C and 7D are schematic illustrations of actual images including features corresponding to the scattering phenomena of a surface, also in accordance with another embodiment of the disclosed technique.
Figure 7E:
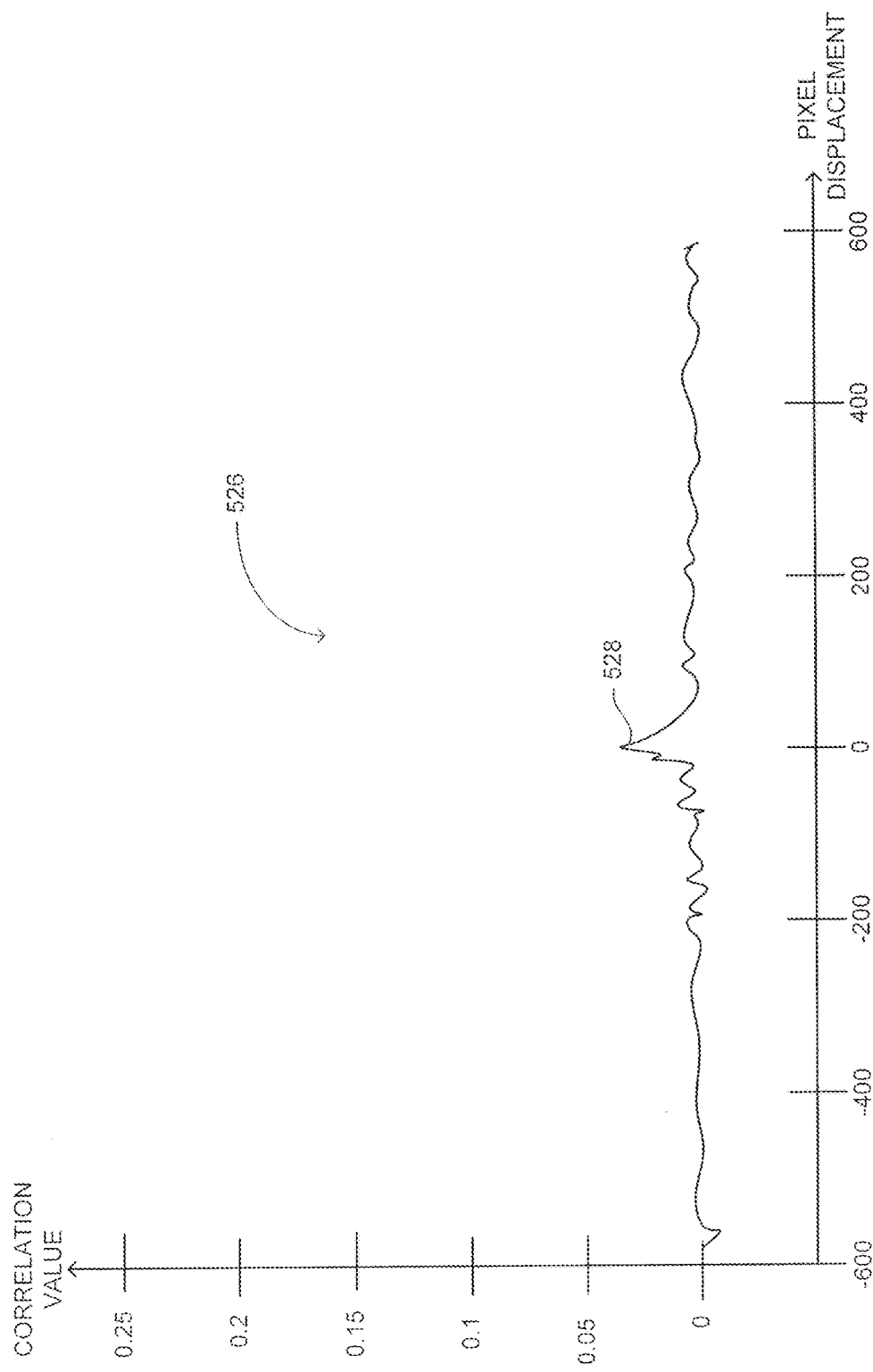
FIG. 7E is a schematic illustration of a graph exhibiting a correlation function, between images also in accordance with another embodiment of the disclosed technique.

As mentioned above, the image features corresponding to the scattering phenomena may change with the relative orientation between the system and the authentication region. More specifically, the image features corresponding to the scattering phenomena may change with the orientation of the authentication region relative to the direction from which the light impinges on the authentication region. To illustrate this phenomena reference is now made to FIGS. 7A, 7B, 7C, 7D and 7E. FIGS. 7A and 7B are schematic illustrations of images including features corresponding to the scattering phenomena, generally referenced 500 and 502, in accordance with another embodiment of the disclosed technique. FIGS. 7C and 7D are schematic illustrations of actual images, generally referenced 522 and 524, including features corresponding to the scattering phenomena of a surface, also in accordance with another embodiment of the disclosed technique. FIG. 7E is a schematic illustration of a graph, generally referenced 526, exhibiting a correlation function 528, between image 522 and image 524 also in accordance with another embodiment of the disclosed technique. Image 500 and 502 are images of the same authentication region. In FIG. 7A, image 500 is acquired when the light, represented by light beam 504 impinges on the authentication region from the same azimuthal direction indicated by arrow 506. Consequently, surface features such as scratches 508 and 510, which are substantially perpendicular to direction 506 appear brighter than scratches 512, 514 and 516 which are substantially parallel to direction 506. Similarly, with reference to FIG. 7B, image 502 was acquired when the light, represented by light beam 518 impinges on the authentication region from the direction indicated by arrow 520. Consequently, scratches 512, 514 and 516, which are substantially perpendicular to direction 520, appear brighter than scratches 508 and 510 which are substantially parallel to direction 516. Thus, if an image was acquired (i.e., the image of the authentication region acquired by a user) when the light was impinging from direction 506, while a corresponding stored image (also referred to herein as a "reference image") was acquired when the light was impinging from direction 520, then these images may be determined not to correspond to each other, thus resulting in a false detection (e.g., the object shall be determined as non-authentic). With reference to FIG. 7E, correlation function 528 is an exemplary result of the correlation between image 522 and 524, for example when image 522 is the reference image (e.g., acquired at the factory producing a product) and image 524 is the authentication image (i.e., the acquired image of the authentication region of the product). As depicted in FIG. 7E, the correlation between these two images is substantially low and the product (i.e., the object to be authenticated) may be determined to be non-authentic.

Figure 7F:
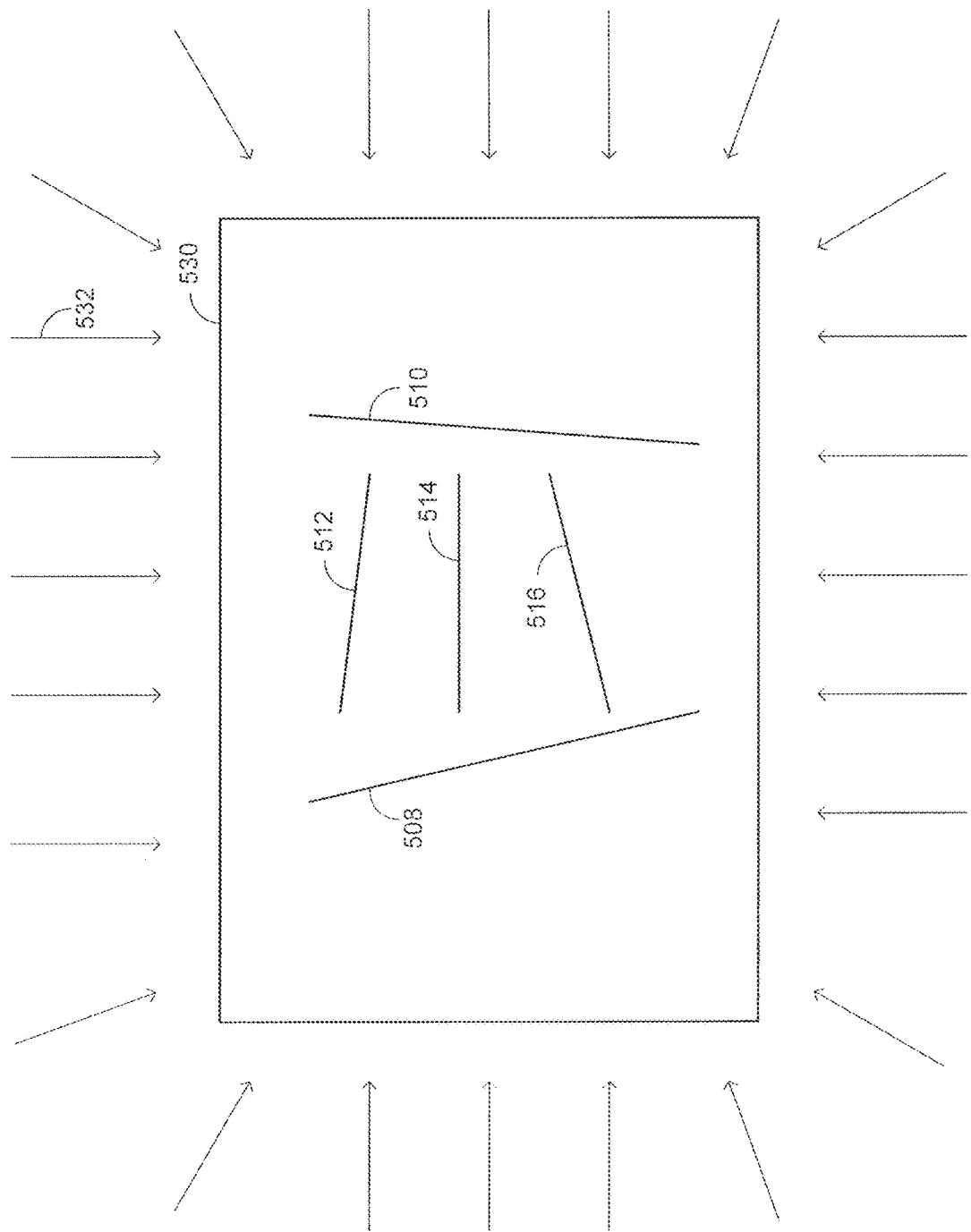
FIG. 7F is a schematic illustration of an image including features corresponding to the scattering phenomena of a surface, in accordance with another embodiment of the disclosed technique.
Figure 7G:
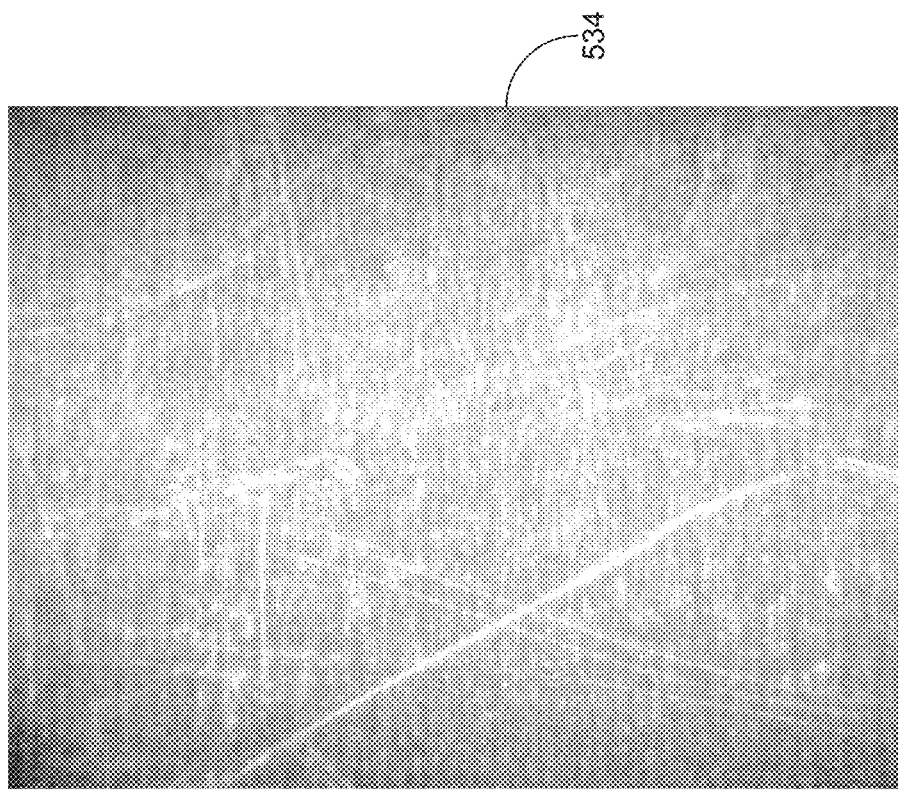
FIG. 7G is a schematic illustrations of an actual image including features corresponding to the scattering phenomena of a surface, also in accordance with another embodiment of the disclosed technique.

To reduce this probability of false detection of a non-authentic object (e.g., by a client inspecting the object with a system for determining authenticity of an object described hereinabove), the stored image is acquired with circumferential lighting. In other words, the reference image is acquired with light impinging on the authentication region circumferentially, from a plurality of different directions. Reference is now made to FIGS. 7F, 7G and 7H. FIG. 7F is schematic illustration of an image, generally referenced 530, including features corresponding to the scattering phenomena of a surface, in accordance with another embodiment of the disclosed technique. FIG. 7G is schematic illustrations of an actual image, generally referenced 534, including features corresponding to the scattering phenomena of a surface, also in accordance with another embodiment of the disclosed technique. FIG. 7H is a schematic illustration of a graph, generally referenced 536, exhibiting a correlation function 538, between image 534 and image 524 also in accordance with another embodiment of the disclosed technique.

In FIG. 7F, circumferential light, represented by light beam 532, impinges on the authentication region circumferentially. Consequently, scratches 508, 510, 512, 514 and 516 all appear with substantially equal brightness. With reference to FIG. 7H, correlation function 538 is an exemplary result of the correlation between image 534 and image 524, for example when image 534 is the reference image and image 524 is the authentication image. As depicted in FIG. 7H, the correlation between these two images is substantially high and the product may be determined to be authentic.

In general, to produce circumferential collimated light (i.e., which impinges on the authentication region from a plurality of direction), an annular light source is employed. According to the disclosed technique, the light produced by this annular light source is also collimated or telecentric light. The annular light source directs the circumferential light toward the authentication region at a predetermined oblique angle relative to the normal of a plane defined by said object as described above in conjunction with FIGS. 2A-2C. Furthermore, also as described above, the region defined by the imaging sensor and a specular reflection region are mutually exclusive in space (i.e., the region defined by the imaging sensor and a specular reflection region do not overlap).

Figure 8:
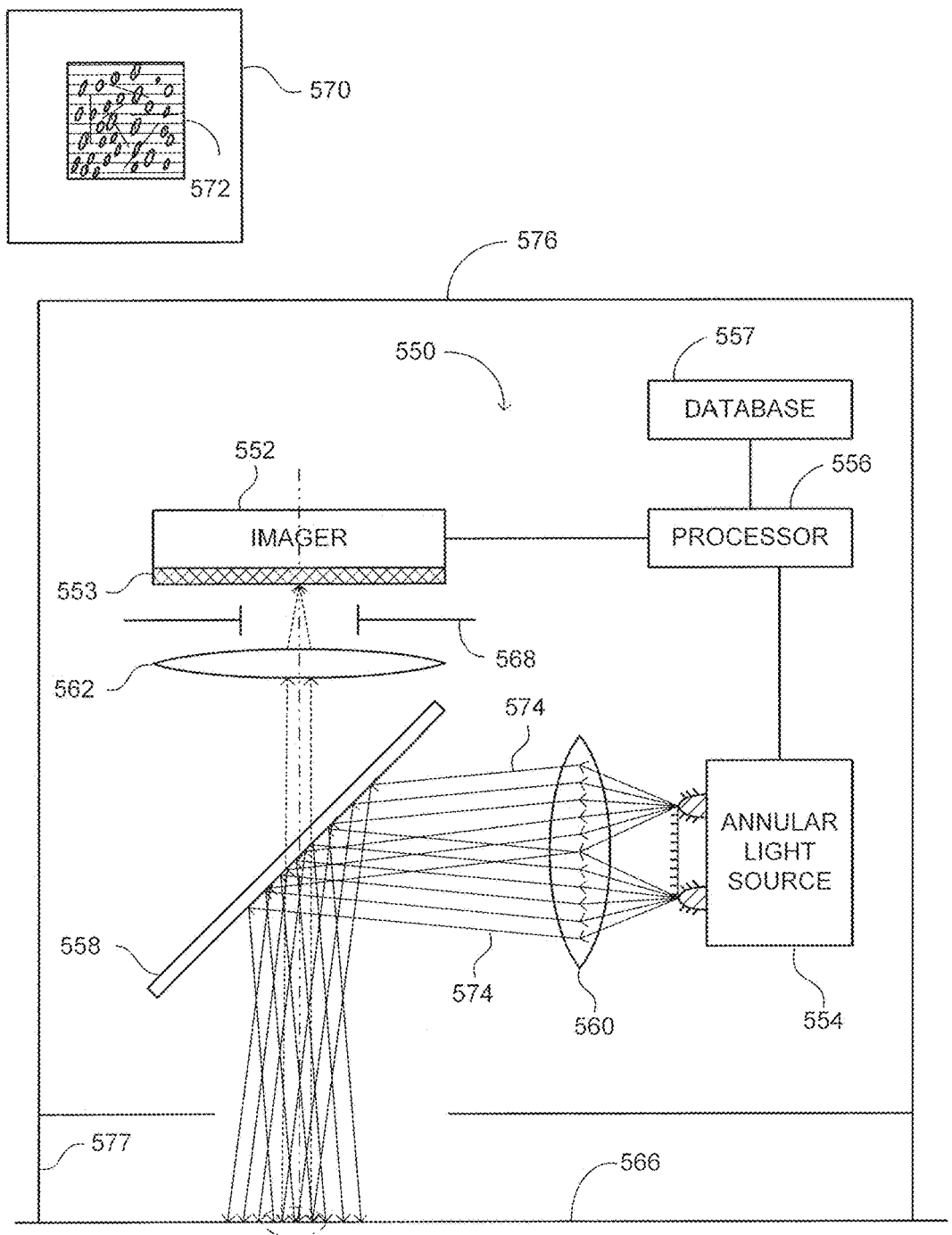
FIG. 8 is a schematic illustration of a system for acquiring a reference image for object authenticity detection, constructed and operative in accordance with a further embodiment of the disclosed technique.

Reference is now made to FIG. 8 which is a schematic illustration of a system, generally referenced 550, for acquiring a reference image for object authenticity detection, constructed and operative in accordance with a further embodiment of the disclosed technique. System 550 is employed in a reference image acquisition module employed when a reference image is to be acquired. System 550 includes an imager 552, an annular light source 554, a database 557. System 550 optionally includes a processor 556. Imager 552 includes an imaging sensor 553. System 550 includes light source optics 560 and imaging optics 562. Optionally, system 550 further includes a beamsplitter 558 and an aperture 568. Processor 556 is coupled with imager 552, with annular light source 554 and with database 557. Light source optics 560 is optically coupled with light source 554 and with beamsplitter 558. Imaging optics 562 is optically coupled with imager 552 and with beamsplitter 558. Light source optics 560 is either collimating optics or telecentric optics. In FIG. 8, aperture 568 is depicted as being located between imaging optics 562 and imager 552. However, aperture 568 may alternatively be located at other positions defined as aperture stop positions (e.g., between imaging optics 562 and beamsplitter 568).

Annular light source 554, directs circumferential light through light source optics 560 toward beamsplitter 558. Light source optics 560 collimates the annular light passing there through, such that collimated light, such as light beam 574 (i.e., which is a circumferential light beam) is directed toward beamsplitter 558. Beamsplitter 558 deflects the circumferential light from light source 554 toward the surface 566 of an authentication region of an object. The circumferential parallel beam impinge on surface 566 at an oblique angle relative to the normal of the object plane at the authentication region from a plurality of different azimuthal directions. The oblique impingement angle of the light is determined according to the diameter of annular light source 554 and the effective focal length of the light source optics 560. For example, when the effective focal length of the light source optics 560 is f and the diameter of the annular light source 554 is H, then the impingement angle, β, of the light on the surface 566 is given by:

$$\beta = \tan^{-1}\left(\frac{H}{2f}\right) \quad (4)$$

The various possible oblique angle values are determined similar to as described above in conjunction with FIG. 2B. Typically, system 550 is housed within a housing 576. Housing 576 may include a stop, such as stop 577, which maintains the distance between surface 566 and sensor 553 at a predetermined distance (i.e., the focal length, f). Stop 577 may exhibit a circular shape, a polygonial shape or may include three or more legs.

Similar to as described above in conjunction with FIGS. 2A-2C, the light impinges on surface 566 circumferentially. A portion of the circumferential light is scattered and another portion is reflected (i.e., specularly reflected). The specularly reflected light defines a specular reflection region, through which specular reflected light propagates (i.e., similar to specular reflection region 164—FIG. 2A). The region defined by imaging sensor 553 and the specular reflection region are mutually exclusive in space. According to one example, aperture 568 blocks the specular reflected light from impinging on imaging sensor 553. Alternatively, imager 552 is positioned such that specular reflection region and the region defined by imaging sensor 503 do not overlap and the specular reflected light does not impinge on imaging sensor 503. Consequently, imager 552 acquires an image of surface 566 resulting only from light scattered from surface 566.

Imager 552 may store the acquired reference image directly into database 557. However, imager 552 may provide the acquired reference image to processor 556. Processor may perform image processing operations such as filtering, histogram equalization, image compression and the like.

Figure 9B:
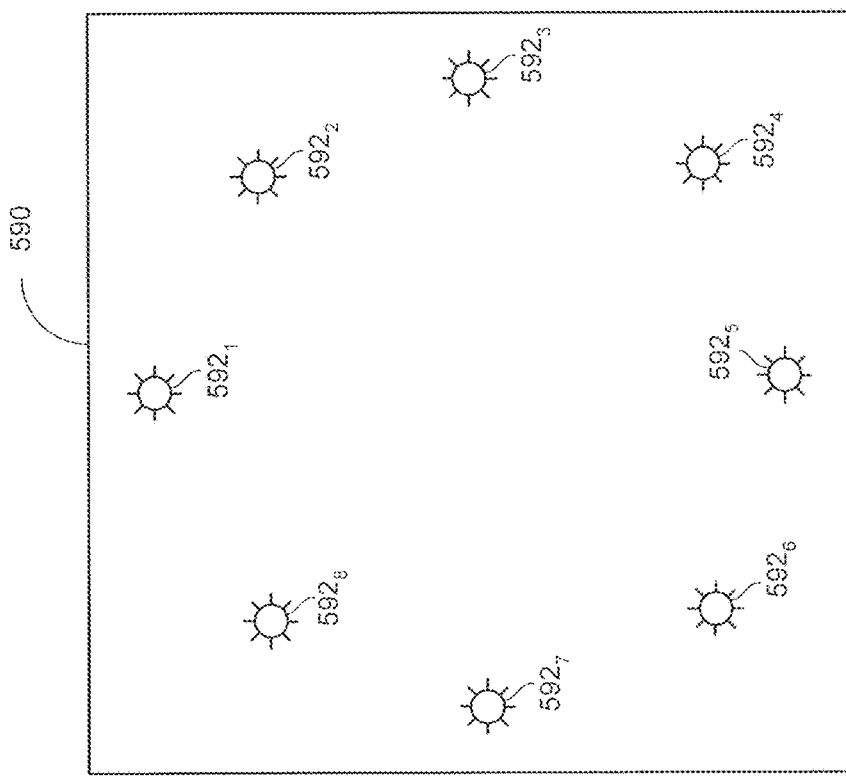
FIG. 9B is a schematic illustration of an annular light source constructed and operative in accordance with a further embodiment of the disclosed technique.
Figure 9A:
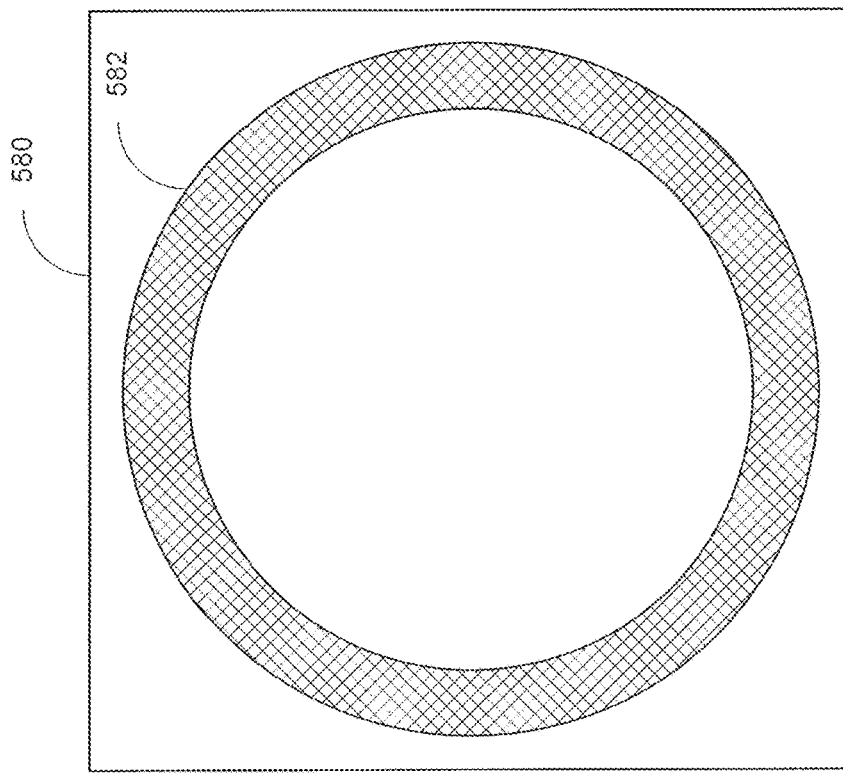
FIG. 9A is a schematic illustration of an annular light source constructed and operative in accordance with another embodiment of the disclosed technique.

It is noted annular light source 554 may be embodied as a single ring shaped light source or a plurality of discrete light source arrange annularly. Reference is now made to FIG. 9A, which is a schematic illustration of an annular light source, generally referenced 580, constructed and operative in accordance with another embodiment of the disclosed technique. Annular light source 580 includes a single ring shaped light source 582. Such a ring shaped light source may be implemented, for example, as a planar light source (e.g., in the shape of a circle) with an opaque mask attached thereon. The area of the mask is smaller than the area of the light source. Furthermore, the mask is attached such that the uncovered area exhibits the shape of a ring. Reference is now made to FIG. 9B, which is a schematic illustration of an annular light source, generally referenced 590, constructed and operative in accordance with a further embodiment of the disclosed technique. Annular light source 590 includes a plurality of discrete light sources. In FIG. 9B, annular light source 590 includes, for example eight discrete light source $592_1$, $592_2$, $592_3$, $592_4$, $592_5$, $592_6$, $592_7$ and $592_8$. Light sources $592_1$-$592_8$ are arranged in a circle. Light sources $592_1$-$592_8$ may be illuminating simultaneously or sequentially. When light sources $592_1$-$592_8$ are illuminating sequentially, the illuminating cycle may be completed during a single exposure of the imager. Alternatively, an image is acquired for each illuminated light source of light sources $592_1$-$592_8$. Thus, each object is associated with eight reference images and each image is associated with a respective different illumination direction. It is noted that eight light source are brought herein as an example only. More than eight or less than eight light sources may be employed. It is further noted that arranging light sources $592_1$-$592_8$ in a circle is also brought herein as an example only. Light sources $592_1$-$592_8$ may also be arrange, for example, in a square, triangle, quadrangle, ellipse and the like.

Figure 9C:
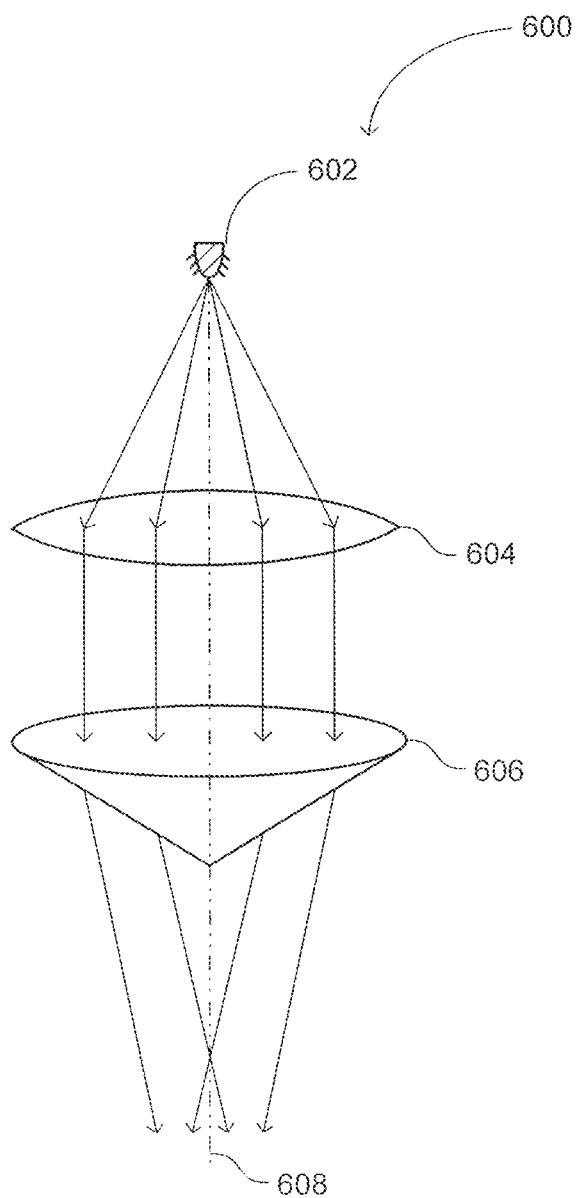
FIG. 9C is a schematic illustration of a light source constructed and operative in accordance with another embodiment of the disclosed technique.

Reference is now made to FIG. 9C, which is a schematic illustration of a light source, generally referenced 600, constructed and operative in accordance with another embodiment of the disclosed technique. Light source 600 includes a single light source 602, collimating optics 604 and an axicon 606. Collimating optics 604 is optically coupled with light source 602 and with axicon 606. Light source 602 emits light toward collimating optics 604. Collimating optics 604 collimates the light beams passing there through. Axicon 606 refracts the parallel light beams producing circumferential light beams at a plurality of azimuthal directions. In other embodiment, the parallel beam exiting the collimating optics 604 can be replaced by a collimated laser beam.

As a further example, annular light source may be a single rotating light source which completes a rotation cycle during a single exposure of the imager. Alternatively, a plurality of images are acquired during the rotation cycle of the light source. Thus, each object is associated with a plurality of reference images each image is associated with a respective different illumination direction.

It will be appreciated by persons skilled in the art that the disclosed technique is not limited to what has been particularly shown and described hereinabove. Rather the scope of the disclosed technique is defined only by the claims, which follow.

The invention claimed is:

1. A system for determining an authenticity of an object comprising:
   a reference image acquisition module for acquiring a reference image for object authenticity detection, the reference image acquisition module including:
   a light source, directing circumferential light toward an authentication region on said object, said circumferential light being at least one of collimated and telecentric, said circumferential light impinging on said authentication region from a plurality of different azimuthal directions and at a predetermined oblique angle relative to a normal of a plane defined by said object, a portion of said circumferential light being reflected from said authentication region toward a specular reflection region, another portion of said circumferential light being scattered from said authentication region;

an imager including an imaging sensor, said imager being focused on said authentication region, said imager acquiring at least one reference image, said reference image being a focused image of said scattered light, said image at least including image features related to surface features scattering phenomena of said authentication region, said specular reflection region and a region defined by said imaging sensor are mutually exclusive in space; and a database, coupled with said imager for storing said reference image.

2. The system according to claim 1, wherein said light source includes a ring shaped light source.

3. The system according to claim 1, wherein said light source includes a plurality of discrete light sources arranged in a circle.

4. The system according to claim 1, wherein said light source includes at least one light emitting diode, collimated optics and an axicon, said collimated optics optically coupled with said light emitting diode and said axicon, said light emitting diode emits light toward said collimated optics, said collimated optics collimate light beams passing there through, said axicon refracts the parallel light beams producing circumferential light beams at a plurality of azimuthal directions.

5. The system according to claim 1 further including a processor for processing the acquired reference image.

6. The system according to claim 5, wherein, said processing includes at least one of filtering, histogram equalization and image compression.

7. The system according to claim 1 being located within a housing, said housing includes stops maintaining the distance between said object and said sensor at a predetermined distance.

8. The system according to claim 1, further including imaging optics optically coupled with imager.

9. The system according to claim 1 further including an aperture located between said imager and said object for blocking specular reflected light from impinging on said imaging sensor.

10. The system according to claim 1 further including a beamsplitter optically coupled with said light source and with said imager, said beamsplitter deflects the light emitted by said light source toward said authentication region at said predetermined oblique angle.

11. The system according to claim 1 further including light source optics optically coupled with light source and with a beamsplitter, said light source optics being one of collimated optics and telecentric optics.

12. The system according to claim 1, wherein said system further including a user module, said user module including:

a light source, directing light toward an authentication region on said object, said light being at least one of collimated and telecentric, said light impinging on said authentication region at a predetermined oblique angle relative to the normal of a plane defined by said object, a portion of said light being reflected from said authentication region toward a specular reflection region, another portion of said light being scattered from said authentication region;

an imager including a imaging sensor, said imager being focused on said authentication region, said imager acquiring at least one focused image of said scattered light, said image at least including image features related to surface features scattering phenomena of said authentication region, said specular reflection region and a region defined by said imaging sensor are mutually exclusive in space; and a processor coupled with said imager, said processor determining correspondence between at least a part of said at least one acquired image and a corresponding part of at least one stored image, said at least one stored image also corresponding to said authentication region, wherein said processor identifies said object as authentic when said at least a part of said acquired image corresponds to said corresponding part of said at least one stored image, wherein said processor identifies said object as non-authentic when said at least a part of said acquired image does not correspond to said corresponding part of said at least one stored image, and wherein said oblique angle (θ) is determined such that said scattered light coherently interferes at the sensor plane.

13. A system for acquiring a reference image for object authenticity detection, the system comprising:

an light source, directing circumferential light toward an authentication region (566) on said object, said circumferential light being at least one of collimated and telecentric, said circumferential light impinging on said authentication region from a plurality of different azimuthal directions and at a predetermined oblique angle relative to a normal of a plane defined by said object, a portion of said circumferential light being reflected from said authentication region toward a specular reflection region, another portion of said circumferential light being scattered from said authentication region;

an imager including a imaging sensor, said imager being focused on said authentication region, said imager acquiring at least one reference image, said reference image being a focused image of said scattered light, said image at least including image features related to surface features scattering phenomena of said authentication region, said specular reflection region and a region defined by said imaging sensor are mutually exclusive in space; and a database coupled with said imager, for storing said reference image.

* * * * *